(12) United States Patent
Lee et al.

(10) Patent No.: US 12,247,063 B2
(45) Date of Patent: Mar. 11, 2025

(54) CELL SURFACE MODIFICATION BY COATING WITH PEPTIDE AMPHIPHILES (PAs)

(71) Applicant: Northwestern University, Evanston, IL (US)

(72) Inventors: Slgirim Lee, Seongnam-si (KR); Samuel I. Stupp, Chicago, IL (US); Lewis Fraser, Chicago, IL (US)

(73) Assignee: Northwestern University, Evanston, IL (US)

( * ) Notice: Subject to any disclaimer, the term of this patent is extended or adjusted under 35 U.S.C. 154(b) by 247 days.

(21) Appl. No.: 17/373,977

(22) Filed: Jul. 13, 2021

(65) Prior Publication Data
US 2022/0009996 A1    Jan. 13, 2022

Related U.S. Application Data

(60) Provisional application No. 63/051,040, filed on Jul. 13, 2020.

(51) Int. Cl.
| | | |
|---|---|---|
| C07K 14/70 | (2006.01) | |
| A61K 39/00 | (2006.01) | |
| A61P 37/06 | (2006.01) | |
| C07K 14/705 | (2006.01) | |
| C12N 5/0783 | (2010.01) | |

(52) U.S. Cl.
CPC .... *C07K 14/70542* (2013.01); *A61K 39/4611* (2023.05); *A61K 39/4621* (2023.05); *A61K 39/46434* (2023.05); *A61K 39/464466* (2023.05); *A61P 37/06* (2018.01); *C12N 5/0637* (2013.01); *A61K 2239/31* (2023.05); *C07K 2319/00* (2013.01)

(58) Field of Classification Search
CPC ............................ C07K 14/70542; A61P 37/06
See application file for complete search history.

(56) References Cited

U.S. PATENT DOCUMENTS

| | | | |
|---|---|---|---|
| 7,030,167 B2 | 4/2006 | Gunther | |
| 7,371,719 B2 | 5/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,076,295 B2 | 12/2011 | Hulvat et al. | |
| 8,080,262 B2 | 12/2011 | Lee et al. | |
| 8,114,834 B2 | 2/2012 | Hsu et al. | |
| 8,114,835 B2 | 2/2012 | Mata et al. | |
| 8,124,583 B2 | 2/2012 | Stupp et al. | |
| 8,138,140 B2 | 3/2012 | Stupp et al. | |
| 8,236,800 B2 | 8/2012 | Degrado et al. | |
| 8,450,271 B2 | 5/2013 | Shah et al. | |
| 8,512,693 B2 | 8/2013 | Capito et al. | |
| 8,546,338 B2 | 10/2013 | Donners et al. | |
| 8,580,923 B2 | 11/2013 | Stupp et al. | |
| 8,748,569 B2 | 6/2014 | Stupp et al. | |
| 8,772,228 B2 | 7/2014 | Stupp et al. | |
| 9,011,914 B2 | 4/2015 | Wong Po Foo et al. | |
| 9,040,626 B2 | 5/2015 | Chien et al. | |
| 9,044,514 B2 | 6/2015 | Xu et al. | |
| 2008/0226562 A1* | 9/2008 | Groves | A61K 49/0002 424/9.6 |
| 2014/0294730 A1* | 10/2014 | Slack-Davis | A61K 51/088 424/9.2 |
| 2018/0326077 A1* | 11/2018 | Panitch | C08B 37/0069 |

FOREIGN PATENT DOCUMENTS

WO    WO2016168302 A1    10/2016

OTHER PUBLICATIONS

Hendricks et al., 2017, Supramolecular Assembly of Peptide Amphiphiles, Acc Chem Res, 50: 2440-2448.*
Matson et al., 2012, Nanostructure-templated control of drug release from peptide amphiphile nanofiber gels, Soft Matter, 8(13): 3586-3595.*
Toft et al., 2012, Co-Assembled Cytotoxic and Pegylated Peptide Amphiphiles Form Filamentous Nanostructures with Potent Anti-Tumor Activity in Models of Breast Cancer, ACS Nano, 6(9): 7956-7965.*
Sato et al., 2018, Peptide Supramolecular Materials for Therapeutics, Chem Soc Rev, 47(20): 7539-7551.*
Matson et al., 2012, Self-assembling peptide scaffolds for regenerative medicine, Chem Commun, 48(1): 26-33.*
Clemons et al., 2020, Design of materials and supramolecular polymers, Progress in Polymer Science, 111: 101310 (10 pages).*
Yu et al., 2016, Asymmetric Peptide Nanoribbons, Nano Lett, 16: 6967-6974.*
Anderson et al., Inhibition of ICAM-1/LFA-1-mediated heterotypic T-cell adhesion to epithelial cells: design of ICAM-1 cyclic peptides. Bioorg Med Chem Lett. Mar. 22, 2004;14(6):1399-402.
Israelachvili Intermolecular and surface forces; 2nd ed.; Academic: London San Diego, 1992, Table of Contents only (14 pages).
Mayo et al., A recipe for designing water-soluble, beta-sheet-forming peptides. Protein Sci. Jul. 1996;5(7):1301-15.

* cited by examiner

*Primary Examiner* — Amber D Steele
(74) *Attorney, Agent, or Firm* — Rikki A. Hullinger; Casimir Jones, S.C.

(57) ABSTRACT

Provided herein are peptide amphiphiles (PAs). In some embodiments, provided herein are targeting PAs comprising a PA backbone and a targeting moiety. In some embodiments, the peptide amphiphiles are assembled into nanofibers. In some embodiments, provided herein are cells coated with a targeting PA or a nanofiber comprising the same, and methods of use thereof.

13 Claims, 28 Drawing Sheets

Specification includes a Sequence Listing.

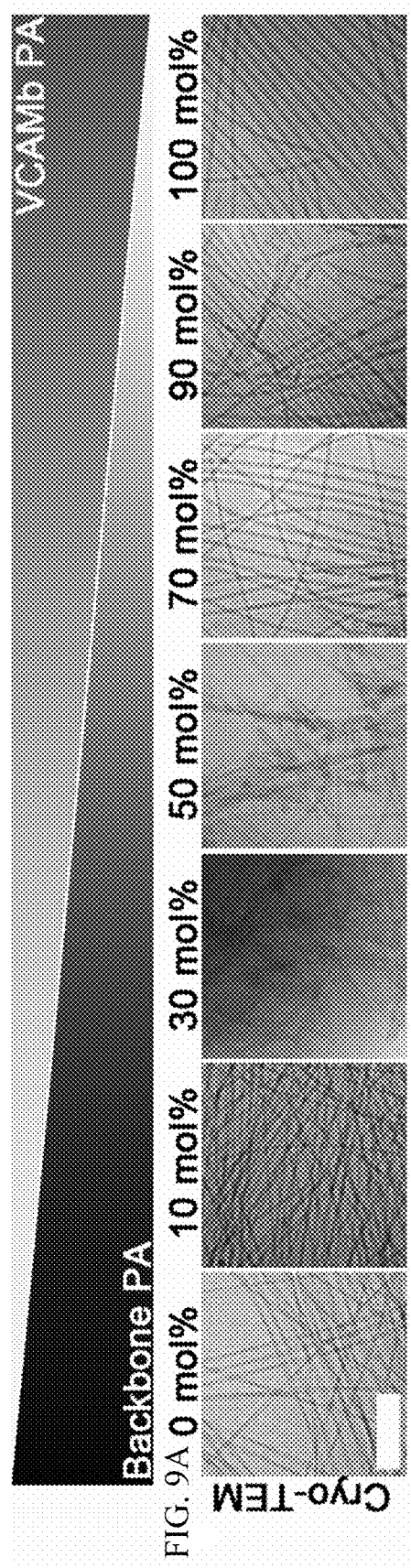
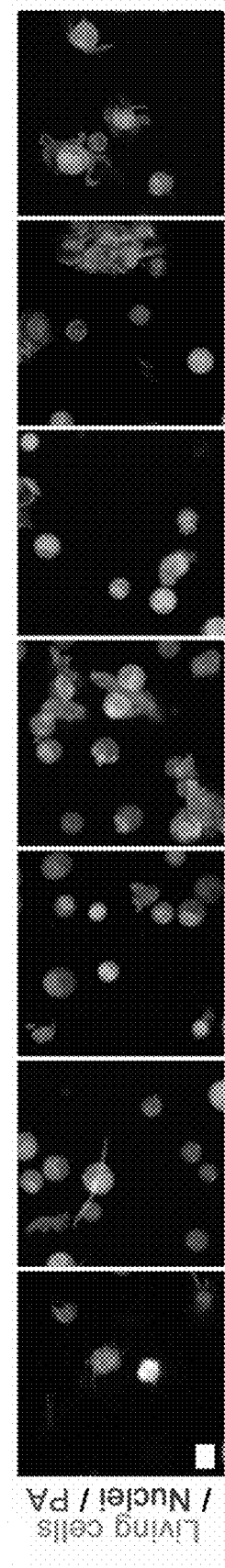
FIG. 9A
FIG. 9B

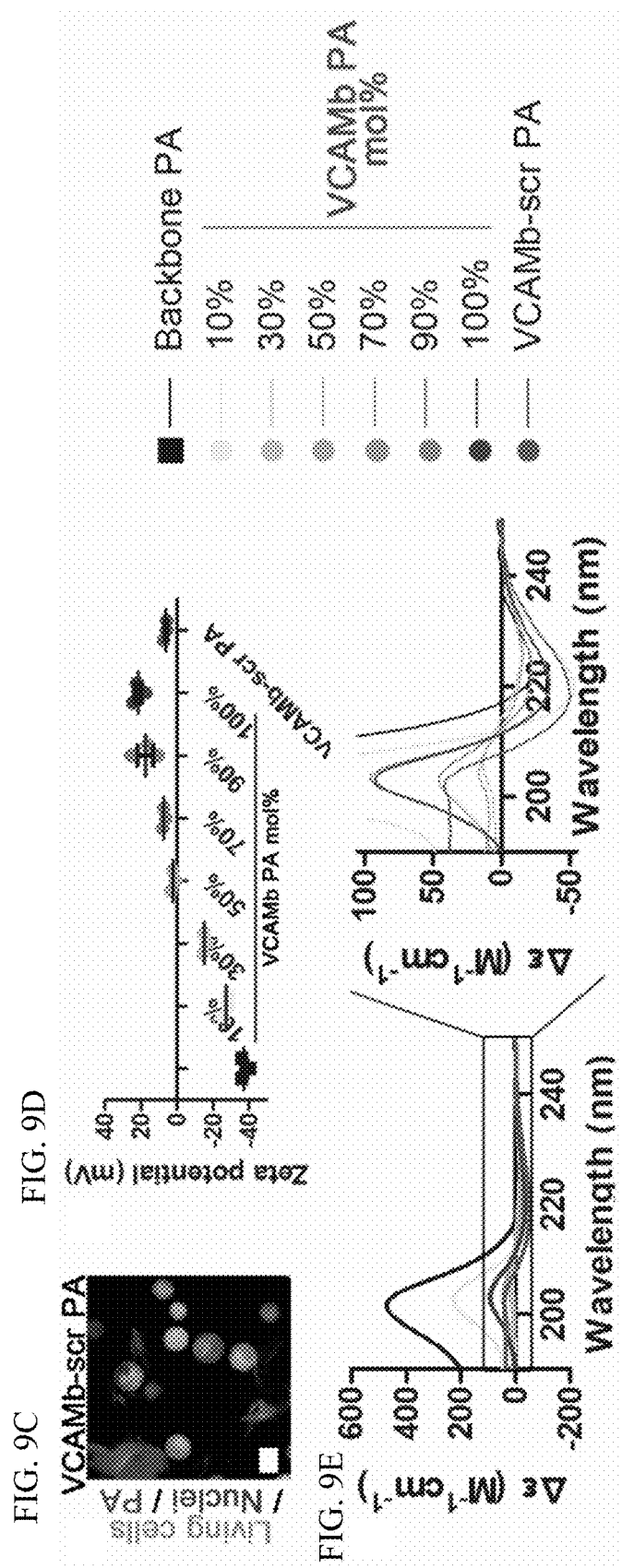

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Val His Pro Lys Gln His
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Asp Val Leu Pro Gly Thr
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Val Val Ala Ala
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Glu Glu Glu Glu
1

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Val Val Val Ala Ala Ala Glu Glu Glu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Val Val Val Ala Ala Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Ala Ala Ala Val Val Val
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Val Val Ala Ala Ala Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Val Val Val Val Ala Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Val Val Ala Ala Glu Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Val His Pro Lys Gln His Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Val Val Val Val Ala Ala Glu Glu Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Val Val Ala Ala Ala Ala Glu Glu Glu
1               5
```

```
<210> SEQ ID NO 14
<211> LENGTH: 18
<212> TYPE: PRT
<213> ORGANISM: Artificial Sequence
<220> FEATURE:
<223> OTHER INFORMATION: Synthetic

<400> SEQUENCE: 14

Val Val Val Ala Ala Ala Glu Glu Glu Gly Ser Gly Val His Pro Lys
1               5                   10                  15

Gln His

<210> SEQ ID NO 15
<211> LENGTH: 19
<212> TYPE: PRT
<213> ORGANISM: Artificial Sequence
<220> FEATURE:
<223> OTHER INFORMATION: Synthetic

<400> SEQUENCE: 15

Val Val Val Ala Ala Ala Glu Glu Glu Gly Ser Gly Val His Pro Lys
1               5                   10                  15

Gln His Arg

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Val His Pro Lys Gln His
1               5

<210> SEQ ID NO 17
<211> LENGTH: 18
<212> TYPE: PRT
<213> ORGANISM: Artificial Sequence
<220> FEATURE:
<223> OTHER INFORMATION: Synthetic

<400> SEQUENCE: 17

Val Val Val Ala Ala Ala Glu Glu Glu Gly Ser Gly Gln His Pro His
1               5                   10                  15

Val Lys

<210> SEQ ID NO 18
<211> LENGTH: 9
<212> TYPE: PRT
<213> ORGANISM: Artificial Sequence
<220> FEATURE:
<223> OTHER INFORMATION: synthetic construct

<400> SEQUENCE: 18

Ala Ala Ala Val Val Val Glu Glu Glu
1               5
```

```
<210> SEQ ID NO 19
<211> LENGTH: 11
<212> TYPE: PRT
<213> ORGANISM: Artificial Sequence
<220> FEATURE:
<223> OTHER INFORMATION: synthetic construct

<400> SEQUENCE: 19

Ile Thr Asp Gly Glu Ala Thr Asp Ser Gly Cys
1               5                   10
```

CELL SURFACE MODIFICATION BY COATING WITH PEPTIDE AMPHIPHILES (PAs)

STATEMENT OF RELATED APPLICATIONS

This application claims priority to U.S. Provisional Patent Application No. 63/051,040, filed Jul. 13, 2020, the entire contents of which are incorporated herein by reference.

SEQUENCE LISTING

The text of the computer readable sequence listing filed herewith, titled "2024-05-16_38510.252_SQL_ST25", created May 16, 2024, having a file size of 3,788 bytes, is hereby incorporated by reference in its entirety.

FIELD

Provided herein are peptide amphiphiles (PAs). In some embodiments, provided herein are targeting PAs comprising a PA backbone and a targeting moiety. In some embodiments, the peptide amphiphiles are assembled into nanofibers. In some embodiments, provided herein are cells coated with a targeting PA or a nanofiber comprising the same, and methods of use thereof.

BACKGROUND

Therapy using living therapeutic cells is a rapidly growing area of research interest[1] with great promise in the ability to treat diseases which currently have no cure or poor outcomes with traditional therapeutics. The concept of cell surface decoration including single cell encapsulation, as well as chemical and biological cell surface modification[2-13] has gathered increasing attention in recent years for its great potential to solve the challenges with the conventional cell therapy systems, such as in vitro formulation of complicated microtissue[11], improved cell retention rate[2] and cell viability after administration[14, 15] and targeted cell delivery to specific lesions[5, 7]. However, these attempts still suffer from inherent challenges such as using the need for highly specialized equipment, the use of animal- or other human-derived or potentially cytotoxic materials, or direct chemical reactions on the therapeutic cells surface. Additionally, there would be issues associated with additional chemical synthesis on the systems in order to assign the specific bioactive functions to the decorating materials. Accordingly, there remains a need for effective methods for decorating the cell surface in order to allow for targeted cell delivery to specific areas within a subject.

SUMMARY

In some aspects, provided herein are peptide amphiphiles. In some embodiments, provided herein are peptide amphiphiles comprising a hydrophobic tail, a structural peptide segment, and a charged peptide segment. In some embodiments, the peptide amphiphile further comprises a targeting moiety. In some embodiments, the targeting moiety comprises the amino acid sequence VHPKQH (SEQ ID NO: 1). In some embodiments, the targeting moiety comprises the cyclic peptide Cyclo(1,12)PenITDGEATDSGC (SEQ ID NO: 19) (cLABL). In some embodiments, the targeting moiety comprises a saccharide. For example, the targeting moiety may comprise a monosaccharide consisting of GlcA, GlcNAc, GlcNS, IdoA, or sulfated versions thereof. In some embodiments, the targeting moiety comprises the amino acid sequence RDVLPGT (SEQ ID NO: 2).

In some embodiments, the hydrophobic tail comprises an 8-24 carbon alkyl chain ($C_{8-24}$). In some embodiments, the structural peptide segment has a propensity for forming β-sheet conformations. For example, the structural peptide segment may comprise $V_2A_2$ (SEQ ID NO: 3). In some embodiments, the charged peptide segment comprises EE, EEE, or EEEE (SEQ ID NO: 4).

The targeting moiety may be attached to the charged peptide segment by a linker. In some embodiments, the linker is a tripeptide linker (e.g., GSG).

In some embodiments, the PA comprises $C_{8-24}$-$V_3A_3E_3$ (SEQ ID NO: 5)-(GSG)-VHPKQH (SEQ ID NO: 1). In some embodiments, the PA comprises $C_{8-24}$-$V_3A_3E_3$ (SEQ ID NO: 5)-(GSG)-cLABL. In some embodiments, the PA comprises $C_{8-24}$-$V_3A_3E_3$(SEQ ID NO: 5)-(GSG)-RDVLPGT (SEQ ID NO: 2).

In some aspects, provided herein are nanofibers comprising the peptide amphiphiles described herein. In some embodiments, provided herein are nanofibers comprising a targeting peptide amphiphile (e.g. a peptide amphiphile comprising a hydrophobic tail, a structural peptide segment, a charged peptide segment, and a targeting moiety). In accordance with any of the embodiments described herein, the nanofiber may further comprise one or more filler peptide amphiphiles. The filler peptide amphiphiles comprise a hydrophobic tail, a structural peptide segment, and a charged peptide segment, and do not comprise a targeting moiety.

In some aspects, provided herein cells comprising a peptide amphiphile as described herein. In some embodiments, provided herein are cells comprising a peptide amphiphile, wherein the peptide amphiphile includes a hydrophobic tail, a structural peptide segment, and a charged peptide segment, and wherein the peptide amphiphile coats at least a portion of an outer surface of the cell. In some embodiments, the hydrophobic tail comprises an 8-24 carbon alkyl chain ($C_{8-24}$). In some embodiments, the structural peptide segment has a propensity for forming β-sheet conformations. For example, the structural peptide segment may comprise $V_3A_3$ (SEQ ID NO: 6). In some embodiments, the charged peptide segment comprises EE, EEE, or EEEE (SEQ ID NO: 4).

In some embodiments, the peptide amphiphile further comprises a targeting moiety. For example, the targeting moiety may comprise the amino acid sequence VHPKQH (SEQ ID NO: 1). As another example, the targeting moiety may comprise the cyclic peptide cLABL. As another example, the targeting moiety may comprise a saccharide (e.g. a monosaccharide, disaccharide, or oligosaccharide). For example, the targeting moiety may comprise a monosaccharide consisting of GlcA, GlcNAc, GlcNS, IdoA, or sulfated versions thereof. As another example, the targeting moiety comprises the amino acid sequence RDVLPGT (SEQ ID NO: 2).

The targeting moiety may be attached to the charged peptide segment by a linker. For example, the linker may comprise the amino acid sequence GSG. In some embodiments, the cell comprises the peptide amphiphile $C_{8-24}$-$V_3A_3E_3$ (SEQ ID NO: 5)-(GSG)-VHPKQH (SEQ ID NO: 1). In some embodiments, the cell comprises the peptide amphiphile $C_{8-24}$-$V_3A_3E_3$(SEQ ID NO: 5)-(GSG)-cLABL. In some embodiments, the cell comprises the peptide amphiphile $C_{8-24}$-$V_3A_3E_3$(SEQ ID NO: 5)-(GSG)-RDVLPGT (SEQ ID NO: 2). In some embodiments, the peptide amphiphile coats at least 75% of the outer surface of the cell. In some embodiments, the peptide amphiphile coats at least 90% of the outer surface of the cell. In some embodiments, the cell is a regulatory T-cell.

In some aspects, provided herein are compositions comprising a cell as described herein.

In some aspects, provided herein are methods of treating and/or preventing transplant rejection in a subject. The methods comprise providing to the subject a composition comprising a cell as described herein (e.g. a cell comprising a peptide amphiphile, such as a targeting peptide amphiphile).

BRIEF DESCRIPTION OF THE DRAWINGS

(FIG. 1A) Schematic description of the experimental procedure for coating and the system. (FIG. 1B) Schematic representation of PA nanofibers with and without biofunctional moieties. The PA with biofunctional motifs shows the exemplary VCAM-1 binding motif VHPKQH (SEQ ID NO: 1) (FIG. 1C) Confocal micrographs showing the PA nanofiber-mediated cell coating technique could be applied to a variety of lineages of cells. Scale bar is 20 μm. Reconstructed 3D confocal images (FIG. 1D) and SEM images (FIG. 1E) of human Treg cells with and without PA-coating. Reconstruct FIG. 13A-D. In vitro assessment of PA matrix coated hTregs.

(FIG. 14A) An ischemic reperfusion surgery was performed on the kidneys of two mice. The blood supply to the left kidney was clamped and then released to model an ischemic reperfusion injury. Mouse Tregs coated in PA ($C_{16}$-$V_3A_3E_3$(SEQ ID NO: 5)) were injected systemically via mouse tail following clamp release. (FIG. 14B) Dissociated mouse kidney cells were analyzed by flow cytometry, the tamara signal provided by the PA co-assembly was observed.

(FIG. 15A) Confocal images of primary splenocytes coated with TAMRA-labeled ICAMb PA displayed high coating efficiency. (FIG. 15B) Flow cytometry of coated primary murine splenocytes displayed little difference between VCAMb and ICAMb PA coating efficiency. (FIG. 15C) Microfluidic flow experiments demonstrated improved retention of coated lymphocytes on the target protein surface (ICAMb PA on ICAM surface, right panels), while non-specific interactions were minimal for off-target proteins (VCAMb PA on ICAM surface, left panels). This can be visualized through both light microscopy (top) and processed images highlighting bound cell edges (bottom).

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms “a”, “an” and “the” include plural reference unless the context clearly dictates otherwise. Thus, for example, reference to “a peptide amphiphile” is a reference to one or more peptide amphiphiles and equivalents thereof known to those skilled in the art, and so forth.

As used herein, the term “comprise” and linguistic variations thereof denote the presence of recited feature(s), element(s), method step(s), etc. without the exclusion of the presence of additional feature(s), element(s), method step(s), etc. Conversely, the term “consisting of” and linguistic variations thereof, denotes the presence of recited feature(s), element(s), method step(s), etc. and excludes any unrecited feature(s), element(s), method step(s), etc., except for ordinarily-associated impurities. The phrase “consisting essentially of” denotes the recited feature(s), element(s), method step(s), etc. and any additional feature(s), element(s), method step(s), etc. that do not materially affect the basic nature of the composition, system, or method. Many embodiments herein are described using open “comprising” language. Such embodiments encompass multiple closed “consisting of” and/or “consisting essentially of” embodiments, which may alternatively be claimed or described using such language.

The term “amino acid” refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine (“naph”), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine (“tBuG”), 2,4-diaminoisobutyric acid, desmosine, 2,2'-diaminopimelic acid, 2,3-diaminopropionic acid, N-ethylglycine, N-ethylasparagine, homoproline (“hPro” or “homoP”), hydroxylysine, allo-hydroxylysine, 3-hydroxyproline (“3Hyp”), 4-hydroxyproline (“4Hyp”), isodesmosine, allo-isoleucine, N-methylalanine (“MeAla” or “Nime”), N-alkylglycine (“NAG”) including N-methylglycine, N-methylisoleucine, N-alkylpentylglycine (“NAPG”) including N-methylpentylglycine. N-methylvaline, naphthylalanine, norvaline (“Norval”), norleucine (“Norleu”), octylglycine (“OctG”), ornithine (“Orn”), pentylglycine (“pG” or “PGly”), pipecolic acid, thioproline (“ThioP” or “tPro”), homoLysine (“hLys”), and homoArginine (“hArg”).

The term “amino acid analog” refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term “peptide” refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

Figure 1A:
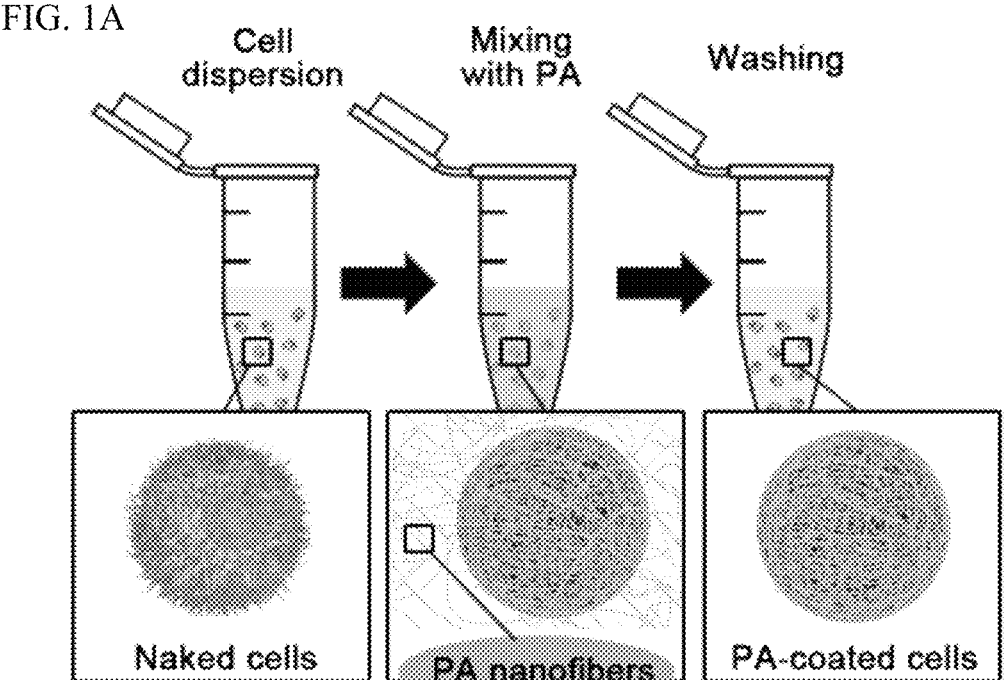
FIG. 1A-E. Supramolecular peptide amphiphile (PA) nanofiber-mediated cell surface decoration.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "glycomimetic" refers to molecular entities that exhibit structural and/or physical properties similar to carbohydrates and/or that exhibit similar or improved binding activity, biological activity, and/or stability. As used herein, the term "fucodian" or "sulfated fucodian" refers to sulfated di-, oligo-, or polysaccharides hat have a backbone built of (1-3)-linked α-1-fucopyranosyl or of alternating (1→3)- and (1→4)-linked α-1-fucopyranosyl residues, but also include sulfated galactofucans with backbones built of (1→6)-P-d-galacto- and/or (1→2)-P-d-mannopyranosyl units with fucose or fuco-oligosaccharide branching, and/or glucuronic acid, xylose or glucose substitutions. There are at least two distinct forms of fucoidan: F-fucoidan, which is >95% composed of sulfated esters of fucose, and U-fucoidan, which is approximately 20% glucuronic acid. Carbohydrate mimetics include, but are not limited to, aza-sugars, c-glycosides, carbasugars, thiosugars, thioglycosides, sulfosugars, iminosugars, phospha sugars, glycosylamines, lactones, pseudo-sugars, aminocyclitols, cyclitols, polyols, inositols such as wyo-inositol and scy/Zo-inositols.

As used herein, the term "nanofiber" refers to an elongated or threadlike filament (e.g., having a significantly greater length dimension that width or diameter) with a diameter typically less than 100 nanometers.

As used herein, the term "scaffold" refers to a material capable of supporting growth and differentiation of a cell.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both). The peptide amphiphile may express a net charge at physiological pH, either a net positive or negative net charge, or may be zwitterionic (i.e., carrying both positive and negative charges).

The term "peptide amphiphile backbone", "backbone", "PA backbone", or "backbone PA" is used herein to refer to a peptide amphiphile comprising a hydrophobic segment, a structural peptide segment, and a charged peptide segment. Backbone PAs are also referred to interchangeably herein as "filler PAs" or "diluent PAs". The PA backbone may be attached to a targeting moiety to generate a "targeting peptide amphiphile".

Certain peptide amphiphiles consist of or comprise (1) a hydrophobic, non-peptide segment (e.g., comprising an acyl group of six or more carbons), (2) a structural peptide segment; (3) a charged peptide segment, and (4) a targeting moiety segment.

The term "peptide amphiphile" includes a "targeting peptide amphiphile". A "targeting peptide amphiphile" or "targeting PA" refers to a peptide amphiphile containing a non-peptide lipophilic (hydrophobic) segment, a structural peptide segment and/or charged peptide segment, and a targeting moiety.

As used herein and in the appended claims, the term "lipophilic moiety" or "hydrophobic moiety" refers to the moiety (e.g., an acyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used interchangeably herein, the terms "structural peptide" or "structural peptide segment" refer to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural peptide segments of adjacent structural peptide segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues). In particular embodiments, the peptide segment is negatively charged.

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the terms "treat," "treatment," and "treating" refer to reducing the amount or severity of a particular condition, disease state (e.g., atherosclerosis), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and preventing" refer to reducing the likelihood of a particular condition or disease state from occurring in a subject not presently experiencing or afflicted with the condition or disease state. The terms do not necessarily indicate complete or absolute prevention. For example, "prevention" refers to reducing the likelihood of a condition or disease state occurring in a subject not presently experiencing or diagnosed with the condition or disease state. In order to "prevent" a condition or disease state, a composition or method need only reduce the likelihood of the condition or disease state, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject (e.g., a PA nanofiber and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

In some aspects, provided herein are peptide amphiphiles (PAs). In some embodiments, provided herein are PAs comprising a targeting moiety (e.g. targeting PAs). In some embodiments, provided herein are nanofibers comprising the targeting PAs described herein. Further provided herein are methods of use of the targeting PAs and nanofibers disclosed herein.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH2, and —NH2.

In some embodiments, peptide amphiphiles comprise a hydrophobic segment (i.e. a hydrophobic tail) linked to a peptide. In some embodiments, the peptide comprises a structural peptide segment. In some embodiments, the structural peptide segment is a hydrogen-bond-forming segment, or beta-sheet-forming segment. In some embodiments, the structural peptide segment has the propensity to form random coil structures. In some embodiments, the peptide comprises a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules may self-assemble (e.g., into cylindrical micelles (a.k.a., nanofibers)) to bury the lipophilic segment in their core. In some embodiments, the targeting PA alone does not self-assemble into a nanofiber. In such cases, the targeting PA may be coassembled with a filler PA (e.g. diluent PA, backbone PA) to induce assembly into a nanofiber formation. In some embodiments, targeting PAs and backbone PAs may coassemble into a nanofiber. In some embodiments, the structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution. In some embodiments, to induce self-assembly one or more diluent PAs may be added to an aqueous solution containing targeting PAs.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE, EEE, or EEEE (SEQ ID NO: 4). For example, in some embodiments an acidic peptide segment comprises EE. In some embodiments, an acidic peptide segment comprises EEE. In other embodiments, an acidic peptide segment comprises EEEE (SEQ ID NO: 4).

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural peptide segment. In some embodiments, the structural peptide segment is a beta-sheet-forming segment. In some embodiments, the structural peptide segment displays weak hydrogen bonding and has the propensity to form random coil structures rather than rigid beta-sheet conformations. In some embodiments, the structural peptide segment is rich in one or more of H, I, L, F, V, G, and A residues. In some embodiments, the structural peptide segment comprises an alanine- and valine-rich peptide segment (e.g., $A_3V_3$ (SEQ ID NO: 7), $V_2A_4$ (SEQ ID NO: 8), $V_3A_3$ (SEQ ID NO: 6), $V_4A_2$ (SEQ ID NO: 9)) or other combinations of V and A residues, etc.). In some embodiments, the structural peptide segment comprises 4 or more consecutive A and/or V residues, or conservative or semi-conservative substitutions thereto. In some embodiments, the structural peptide segment comprises $V_3A_3$ (SEQ ID NO: 6).

In some embodiments, peptide amphiphiles comprise a spacer or linker segment. In some embodiments, the spacer or linker segment is located at the opposite terminus of the peptide from the hydrophobic segment. In some embodiments, the linker segment is a non-peptide linker. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C=O groups (e.g., $CH2(O(CH_2)_2)_2NH$, $CH2(O(CH_2)_2)_2NHCO(CH_2)_2CCH$, etc.). In some embodiments, a spacer or linker further comprises additional bioactive groups, substituents, branches, etc. In some embodiments, the linker segment is a single glycine (G) residue. In some embodiments, the linker segment is a tripeptide linker (e.g. GSG).

In some embodiments, peptide amphiphiles comprise a targeting moiety. Peptide amphiphiles comprising a targeting moiety are referred to herein as "targeting peptide amphiphiles". A targeting moiety may be any suitable moiety that enables targeted delivery of the PA or a cell comprising the same to a desired location. For example, the targeting moiety may be a targeting peptide. In some embodiments, the targeting PA comprises a moiety (e.g. a peptide) that binds to an inflammatory agent, thereby enabling targeted delivery of the PA or a cell comprising the same to a location in a human subject experiencing an inflammatory response. For example, the targeting moiety may comprise a moiety (e.g., a peptide) that binds to an inflammatory agent, thereby enabling targeted delivery of the PA or a cell comprising the same to a transplanted tissue in a subject at risk of or currently experiencing transplant rejection. For example, the targeting moiety may comprise a moiety that binds to an inflammatory agent such as intracellular adhesion molecule 1 (ICAM-1), vascular cell adhesion protein 1 (VCAM-1), cell adhesion molecules (e.g. selectin, cadherins, integrins, Immunoglobulin superfamily CAMs) or inflammatory cytokines including, but not limited to, IFNγ, IL-2, IL-12, TNFα, or GM-CSF.

In some embodiments, the targeting moiety binds to VCAM-1. For example, the targeting moiety may comprise a peptide comprising an amino acid sequence with at least 80% sequence identity (e.g. 80%, 85%, 90%, 91%, 92%, 93%, 94%, 95%, 96%, 97%, 98%, 99%, or 100%) to VHPKQH (SEQ ID NO: 1).

In some embodiments, the targeting moiety binds to ICAM-1. In some embodiments, the targeting moiety binds to ICAM-1 and disrupts the interaction between ICAM-1 and Leukocyte-function associated antigen-1 (LFA-1). LFA-1 is an alpha(L)beta(2) chain integrin expressed on the surface of endothelial cells that modulates the behavior of leukocytes by mediating their adhesion to other cells through its interaction to cell-surface ligands. The interaction between LFA-1 and ICAM-1 is involved in inflammatory responses and is therefore implicated in inflammatory pathologies and autoimmune diseases. For example, the targeting moiety may be a linear peptide or a cyclic peptide derived from ICAM-1 or LFA-1. In some embodiments, the targeting moiety may comprise a cyclic peptide derived from LFA-1. For example, the targeting moiety may comprise the cyclic peptide Cyclo(1,12)PenITDGEATDSGC (SEQ ID NO: 19) (cLABL). In some embodiments, the targeting moiety may comprise a cyclic peptide derived from ICAM-1. Exemplary cyclic peptides derived from ICAM-1 include cIBL, cIBR, cIBC, CH4 and CH7, described in Anderson et al., Bioorg Med Chem Lett. 2004, 22; 14(6), the entire contents of which are incorporated herein by reference. In some embodiments, the targeting moiety (e.g. cLABL, cIBL, cIBR, cIBC, CH4, CH7, etc.) may be modified. For example, the targeting moiety may be modified to increase bioactivity of the targeting moiety, enhance binding to the PA, enhance cell coating ability of a nanofiber, etc.

In some embodiments, the targeting moiety binds to a cell adhesion molecule. For example, the targeting moiety may bind to one or more selectins. The selectins (lectin-EGF-complement binding-cell adhesion molecules [LEC-CAMs]) are a family of mammalian receptors implicated in the initial interactions between leukocytes and vascular endothelia, leading to lymphocyte homing, platelet binding, and neutrophil extravasation. The three known selectins include L-selectin (leukocyte adhesion molecule-1 [LECAM-1]), E-selectin (endothelial-leukocyte adhesion molecule-1 [ELAM-1]), and P-selectin (GMP-140). In some embodiments, the targeting moiety binds to L-selectin. For example, the targeting moiety may comprise a carbohydrate (e.g. a monosaccharide, a disaccharide, or an oligosaccharide). For example, the targeting moiety may comprise a monosaccharide, disaccharide, oligosaccharide, or sulfated version of GlcA, GlcNAc, GlcNS, or IdoA. Exemplary carbohydrates that may be displayed on the surface of a nanofiber and thereby serve as targeting moieties for L-selectin are disclosed in PCT Publication No. WO2016168302A1, the entire contents of which are incorporated herein by reference.

In some embodiments, the targeting moiety binds to Myeloid differentiation primary response protein MyD88 (MyD88). MyD88 is an adapter protein involved in the Toll-like receptor and IL-1 receptor signaling pathway in the innate immune response. MyD88 acts via IRAK1, IRAK2. IRF7 and TRAF6, leading to NF-kappa-B activation, cytokine secretion and the inflammatory response. MyD88 also increases IL-8 transcription and is involved in the IL-18 mediated signaling pathway. In some embodiments, the targeting moiety comprises a peptide comprising an amino acid sequence with at least 80% sequence identity (e.g. 80%, 85%, 90%, 91%, 92%, 93%, 94%, 95%, 96%, 97%, 98%, 99%, or 100%) to RDVLPGT (SEQ ID NO: 2). In some embodiments, the targeting moiety comprises SEQ ID NO: 2.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural peptide segment, targeting moiety, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural peptide segment (e.g., comprising $V_3A_3$ (SEQ ID NO: 6)); and (c) a charged segment (e.g., comprising EE, EEE, EEEE (SEQ ID NO: 4), etc.). In some embodiments, any PAs within the scope described herein, comprising the components described herein, or within the skill of one in the field, may find use herein.

In some embodiments, a targeting peptide amphiphile comprises (e.g., from C-terminus to N-terminus or from N-terminus to C-terminus): targeting moiety (e.g. VHPKQH (SEQ ID NO: 1), RDVLPGT (SEQ ID NO: 2))—charged segment (e.g., comprising EE, EEE, EEEE (SEQ ID NO: 4), etc.)—structural peptide segment (e.g., $V_3A_3$ (SEQ ID NO: 6))—hydrophobic tail (e.g., comprising an alkyl chain of 8-24 carbons).

In some embodiments, a targeting peptide amphiphile comprises (e.g., from C-terminus to N-terminus or from N-terminus to C-terminus): targeting moiety (e.g. VHPKQH (SEQ ID NO: 1), RDVLPGT (SEQ ID NO: 2))—linker (e.g. GSG)—charged segment (e.g., comprising EE, EEE, EEEE (SEQ ID NO: 4), etc.)—structural peptide segment (e.g., $V_3A_3$ (SEQ ID NO: 6))—hydrophobic tail (e.g., comprising an alkyl chain of 8-24 carbons).

In some embodiments, a PA further comprises an attachment segment or residue (e.g., K) for attachment of one or more segments of the PA to another segment. For example, the PA may further comprise a residue for attachment the hydrophobic tail to the peptide portion of the PA. In some embodiments, the hydrophobic tail is attached to a lysine side chain.

In some embodiments, provided herein are nanofibers and nanostructures assembled from any combination of the peptide amphiphiles described herein. In some embodiments, a nanofiber is prepared by the self-assembly of the PAs described herein. In some embodiments, a nanofiber comprises or consists of targeting PAs. In some embodiments, in addition to targeting PAs, filler PAs (e.g. diluent PAs, backbone PAs) are included in the nanofibers. In some embodiments, filler PAs are peptide amphiphiles, as described herein (e.g., structural peptide segment, charged segment, hydrophobic segment, etc.), but lacking a targeting moiety. Filler PAs are also referred to herein as "backbone PAs". In some embodiments, filler PAs are basic or acidic peptides.

In some embodiments, the filler PAs and the targeting PAs self-assemble into a nanofiber.

In some embodiments, filler peptides (e.g., basic peptide, acidic peptides, etc.) impart mechanical characteristics to a material comprising the PA nanofibers described herein. In some embodiments, a nanofiber assembled from 0-75%

(mass %) targeting PA and 25-100% (mass %) basic filler PA becomes a gel at basic pH conditions (e.g., pH 8.5-11). In some embodiments, a nanofiber assembled from 75-100% (mass %) targeting PA and 0-25% (mass %) basic filler PA is a liquid at basic pH conditions (e.g., pH 8.5-11). In some embodiments, a nanofiber assembled from 0-20% (mass %) targeting PA and 80-100% (mass %) acidic filler PA becomes a gel at acidic pH conditions (e.g., pH 1-5). In some embodiments, a nanofiber assembled from 20-80% (mass %) targeting PA and 20-80% (mass %) acidic filler PA becomes a gel at neutral pH conditions (e.g., pH 5-8.5). In some embodiments, a nanofiber assembled from 80-100% (mass %) targeting PA and 0-20% (mass %) acidic filler PA is a liquid at acidic pH conditions (e.g., pH 1-5).

In some embodiments, nanostructures (e.g., nanofibers) comprise 100%, 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) targeting PAs. In some embodiments, nanofibers comprise 100% targeting PAs. In particular embodiments, nanofibers comprise 40% targeting PAs. For example, nanofibers may comprise 40% targeting PAs and 60% filler PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) acidic filler PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) basic filler PAs. In particular embodiments, nanofibers comprise 50% filler PAs.

In some embodiments, the ratio of targeting PAs to acidic and/or basic PAs in a nanofiber determines the mechanical characteristics (e.g., liquid or gel) of the nanofiber material and under what conditions the material will adopt various characteristics (e.g., gelling upon exposure to physiologic conditions, liquifying upon exposure to physiologic conditions, etc.).

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a filler PA. In some embodiments, at least 0.25 mg/mL of the solution is a filler PA. In some embodiments, a filler PA is a PA molecule having highly charged glutamic acid residues on the terminal end of the molecule (e.g., surface-displayed end). These negatively charged PAs allow for the gelation to take place between nanofibers via ionic crosslinks. In some embodiments, a filler PA is a PA molecule having highly charged lysine residues on the terminal end of the molecule (e.g., surface-displayed end). These positively charged PAs allow for the gelation to take place under basic conditions. The filler PAs provide the ability to incorporate other PAs molecules (e.g. targeting PAs) into the nanofiber matrix while still ensuring the ability of the nanofibers solution to gel. In some embodiments, the solutions are annealed for increased viscosity and stronger gel mechanics. These filler PAs have sequences are described in, for example, U.S. Pat. No. 8,772,228 (e.g., $C_{16}$-VVVAAAEEE (SEQ ID NO: 5), e.g., $C_{16}$-VVAAEE (SEQ ID NO: 10)), which is herein incorporated by reference in its entirety.

In some embodiments, the PA nanofiber described herein exhibit a small cross-sectional diameter (e.g., <25 nm, <20 nm, <15 nm, about 10 nm, etc.). In some embodiments, the small cross-section of the nanofibers (~10 nm diameter) allows the fibers to permeate the brain parenchyma.

In some embodiments, provided herein are cells comprising a PA as described herein. In some embodiments, the PA is in the form of a nanofiber as described herein. For example, a cell may be partially or completely coated with a nanofiber comprising a PA as described herein. The cell may be coated with any suitable PA as described herein (e.g. any PA comprising a hydrophobic tail, a structural peptide segment, and a charged peptide segment). In some embodiments, the cell is coated with a targeting PA (e.g. a PA comprising the PA backbone and a targeting moiety) or a nanofiber comprising the same. In some embodiments, the cell may be coated with a filler PA or a nanofiber comprising the same. In some embodiments, the cell may be coated with a nanofiber comprising a targeting PA and a filler PA. The term "coated" indicates that at least a portion of the cell surface is covered by the nanofiber. The term "coated" includes both "partial coating" and "complete coating" with the nanofiber. Successful coating of a cell with a nanofiber as described herein may be confirmed by various techniques, including cryogenic transmission electron microscopy and/or confocal microscopy. The term "partially coated" with a nanofiber indicates that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the cell surface is coated with the nanofiber. The term "completely coated" with a nanofiber indicates that essentially the entire surface of the cell is coated with the nanofiber (e.g. 99% or more of the cell surface is coated with the nanofiber).

Various methods may be employed to coat the desired cell with the nanofiber. In some embodiments, cells may be prepared as a dispersion in a suitable buffer (e.g. DPBS). The cells may be washed using various buffers to remove serum or other proteins from the cell dispersion prior to coating. Cells may be incubated with the targeting PA or a nanofiber comprising the same, the backbone PA or a nanofiber comprising the same, or a nanofiber comprising a targeting PA and/or backbone PA for a suitable duration of time. For example, cells may be incubated with the desired PA and/or nanofiber for about 30 seconds, about 1 minute, about 2 minutes, about 3 minutes, about 4 minutes, about 5 minutes, about 5 minutes, about 7 minutes, about 8 minutes, about 9 minutes, about 10 minutes, or longer than 10 minutes. Suitable steps may be employed after incubation, including centrifugation, aspiration of the supernatant, and one or more wash steps.

Any suitable cell may be coated with a nanofiber as described herein. In some embodiments, the cell may be a human cell. Suitable cells include, for example, immune cells (e.g., granulocytes, mast cells, monocytes, neutrophils, dendritic cells, stem cells, natural killer cells, B cells, T cells, and regulatory T cells (Tregs). In some embodiments, the cell is a regulatory T cell. For example, the cell may be a human regulatory T cell (hTreg). In some embodiments, the cell may be isolated from a subject (e.g. a human subject), coated with a targeting PA or a nanofiber comprising the same, and re-administered to the subject.

In some embodiments, provided herein are compositions comprising a cell that is coated with a nanofiber as described herein. The composition may further comprise one or more pharmaceutically acceptable carriers. For example, the composition may further comprise one or more pharmaceutically acceptable carriers for delivery to a subject.

In some embodiments, the compositions provided herein find use in methods of treating and/or preventing transplant rejection in a subject. For example, provided herein is a method of treating and/or preventing transplant rejection in a subject, comprising providing to the subject a composition comprising a cell coated with a PA as described herein. For example, the methods may comprise providing to the subject a composition comprising a cell coated with a targeting PA as described herein. In some embodiments, the targeting PA comprises a peptide that binds to an inflammatory agent, thereby enabling targeted delivery of cell to a location in a human subject experiencing an inflammatory response. For example, the targeting moiety may comprise a peptide that binds to an inflammatory agent, thereby enabling targeted delivery of the cell to a transplanted tissue in a subject at risk of or currently experiencing transplant rejection.

In some embodiments, the compositions described herein are formulated for delivery to a subject. In some embodiments, the compositions are administered parenterally. The term "parenteral" refers to any suitable non-oral route of administration, including subcutaneous, intramuscular, intravenous, intrathecal, intracisternal, intraarterial, intraspinal, intraepidural, intradermal, and the like. The PA compositions herein can be administered as the sole active agent or in combination with other pharmaceutical agents. For example, the compositions can be administered in combination with other agents for the treatment or prevention of transplant rejection. For example, the compositions can be administered in combination with immunosuppressive drugs (e.g. corticosteroids, calcineurin inhibitors, anti-proliferatives, mTOR inhibitors), antibody-based treatments (e.g. anti-T cell antibodies, anti-IL-2Ra antibodies, anti-CD-20 antibodies), blood transfer, marrow transplants, gene therapy, or other suitable methods for the treatment and/or prevention of transplant rejection in the subject.

EXAMPLES

Example 1

A PA-based supramolecular nanofibrous system for a targeted cell delivery system is described herein. The present disclosure provides a novel cell surface coating technique with PA nanofibers on individual cells with near-100% efficiency. The dynamic and bioactive nanofibers were able to successfully coat the surface of a variety of cell types within minutes and without additional chemical reactions or apparatus, which makes the technique highly amenable to clinical translation. In addition to the characterization and optimization on PA nanofibers utilized in the cell "coating", human regulatory T cells (hTreg cells) were used as a model cell line in order to investigate the potential of the cell delivery system to target protein-rich regions.

Regulatory T cells have recently begun to receive intense attention for their potential application in cancer[34, 35], autoimmune diseases[34], and organ or tissue transplantation[36]. Animal studies have shown that injections of regulatory T cells or Tregs can induce immunologic tolerance. Especially $CD4^+CD25^+FOXP3^+$ Tregs have been found to be elevated in a few human transplant recipients who became tolerant[37-44]. Treg therapy involves harvesting Treg cells, expanding their numbers, then reintroducing them to the patient. For the therapy to be most effective, the Treg cells need to maintain high viability while also be able to migrate to the transplant region. Accordingly, the present example evaluated hTregs coated with PA nanofibers comprising a VCAM-1 targeting moiety.

EXPERIMENTAL SECTION

1. Peptide Amphiphile (PA) Synthesis.

Peptides were synthesized in the Simpson Querrey Institute's Peptide Synthesis Core Facility at Northwestern University. Peptide synthesis was carried out using a CEM Liberty Blue microwave-assisted peptide synthesizer via standard 9-fluorenyl methoxycarbonyl (Fmoc) solid-phase peptide synthesis on rink amide MBHA resin. Peptides were cleaved from the resin using standard solutions (95% TFA, 2.5% water, 2.5% triisopropylsilane (TIS)), precipitated with cold ether and then purified by reverse-phase HPLC on a Waters Prep150 or Shimadzu Prominence HPLC using a water/acetonitrile (each containing 0.1% NH4OH) gradient. Eluting fractions containing the desired peptide were confirmed by mass spectrometry using an Agilent 6520 QTOF LCMS. Confirmed fractions were pooled and the acetonitrile was removed by rotary evaporation before freezing and lyophilization. Purity of lyophilized products was tested by LCMS on an Agilent 6520 QTOF LCMS.

2. Material Characterization 2.1. PA Solution Preparation.

PAs were dissolved in distilled water with pH adjustment to pH 6.5-7.0 using 1N NaOH, if necessary. The stock solution of PA without TAMRA labeling was prepared with 1% concentration. The stock solution of PA with TAMRA (PA-TAMRA) labeling was prepared with 0.1% concentration. PA and PA-TAMRA was mixed with the 99:1 molar ratio and sonicated for 30 minutes. Samples were annealed at 80° C. for 30 minutes and, then slowly cooled down at 1° C./minute to reach 25° C. The final concentration was adjusted by adding DPBS (Gibco).

2.2. Cryogenic Transmission Electron Microscopy (Cryo-TEM).

CryoTEM was performed on a JEOL 1230 at an accelerating voltage of 100 KV equipped with a Gatan 831 CCD camera. PAs were prepared at 10 mM in DPBS diluted to 1 mM immediately prior to vitrification. Samples were pipetted at 7.0 µL volumes onto 300-mesh copper grids with lacey carbon support (Electron Microscopy Sciences) that were treated with glow discharge for 20 seconds. Samples were blotted twice at one second per blot before plunging into liquid ethane using a Vitrobot Mark IV (FEI) vitrification robot operating at room temperature and 95-100% humidity. After vitrification, the samples were transferred under liquid nitrogen to a Gatan 626 cryo-holder for imaging.

2.3. Circular Dichroism (CD).

Immediately before the measurement samples were diluted to 500, 250 and 125 µM with milli-Q $H_2O$ from 10 mM DPBS stocks. CD spectra were recorded on a JASCO model J-815 spectropolarimeter using a quartz cell of 0.5 mm optical path length. Continuous scanning mode was used with a scanning speed of 100 nm per minute with the sensitivity set to standard mode. High Tension (HT) voltage was recorded for each sample to ensure that the measurement was not saturated. An accumulation of 3 measurements was used and a Milli-Q water sample was background-subtracted to obtain final spectra. The serial dilution was used to ensure sample absorption followed Beer-Lambert law. The final spectra were normalized to molar ellipticity using a molar averaged molecular weight of the co-assembled fibers.

2.4. Small Angle X-Ray Scatting (SAXS).

X-ray scattering experiments were performed at Beamline 5-ID-D, DND-CAT, Advanced Photon Source at the Argonne National Laboratory. The solution samples were placed in 1.5 mm quartz capillaries (Charles Supper). An X-ray energy of 17 keV was selected using a double monochromator, and the scattering patterns for water-filled capillaries and sample-filled capillaries were recorded using a set of three charge coupled device (CCD) detectors.[1] The two-dimensional scattering patterns then azimuthally integrated to generate a scattering vector magnitude q vs. intensity plot, where q is defined as $q=4\pi \sin(\theta)/\lambda$ for which $\theta$ denotes the half of total scattering angle and $\lambda$ the X-ray wavelength, 0.7293 Å. 2D to 1D data reduction was performed by GSAS-II software.[2] No attempt was made to determine the absolute scattering intensity due to the variability in quartz capillary diameters.

2.5. Zeta Potential Measurement.

The PA solutions were prepared with the final concentration of 0.1 mM in DPBS. Each solution was transferred to folded capillary zeta cells (Malvern). The zeta potential was measured using zetasizer Nano ZSP (Malvern).

2.6. Biolayer Interferometry (BLI).

The PA solution of each PA were prepared with the concentration 1 mM after annealing and serial dilutions were made for 100, 10, 1 µM, 100, 10, 1 nM solutions using DPBS. Recombinant Human VCAM-1/CD106 Fc chimera protein (R&D Systems) was purchased and the stock solution of 100 µg/mL was prepared according to the manufacturer's instructions and stored in −80° C. until use. For measurement, the protein solution was diluted to 10 µM. The binding responses were measured and recorded by BLItz Bio-Layer Interferometer in Keck Biophysics Facility, Chicago campus, Northwestern University. The biosensor utilized for this study was Anti-Penta-HIS Biosensors (ForteBio). The measuring protocol is as follows: 30 seconds of initial baseline measurement, 600 seconds of protein (VCAM-1) immobilization, 30 seconds of base line measurement, 300 seconds of association measurement, 300 seconds of dissociation measurement. The dissociation constant was calculated by BLItz Pro Software.

3. Biological Assays 3.1. Cell Culture.

3T3 and C2C12 cell lines were cultured in Dulbecco's modified Eagle's medium (DMEM; Invitrogen) with 10% fetal bovine serum (FBS) (Invitrogen) and 1% penicillin and streptomycin (Invitrogen) at 37° C. and 5% $CO_2$. CCRF-CEM cell lines were utilized as a model cell lines for hTreg cells and cultured in RPMI 1640 media (Invitrogen) with 10% FBS and 1% antibiotics.

3.1.1. Isolation and Expansion of Human Regulatory T Cells (Treg Cells).

To isolate the Treg cells, the apheresis product collected from peripheral blood was suspended in a de-clumping buffer (Miltenyi PBS/EDTA Buffer, 25% Human Serum Albumin (HSA), $MgCl_2$, and Pulmozyme). Using CliniMACS Plus and GMP grade reagents, the CD8 and CD19 depletion and CD25+ enrichment was carried out (Miltenyi). The isolated Tregs were stimulated/expanded with Exp-Act® beads at a 4:1 (bead:cell) ratio in a TexMACS medium supplemented with 5% heat-inactivated AB serum, 1,000 IU/ml IL-2, 100 ng/ml Sirolimus (SRL: Rapamycin; Sigma Aldrich) and 1 µg/ml TGF-β (Miltenyi Biotec). The cells were then restimulated with Exp-Act® beads, at a ratio of 1:1 beads on Day 7 and 14. Further, the expanded Tregs were harvested on Day 21 and Exp-Act beads were removed on the CliniMACS Plus instrument for the nanofiber coating experiment and evaluation. Peripheral blood samples were obtained under a protocol following written informed consent approved and supervised by a Northwestern University Institutional Review Board.

3.2. Cell Surface Decoration with PA Nanofibers.

3.2.1. Cell Dispersion Preparation.

The cells for PA nanofiber coating should be prepared as a dispersion in buffer (DPBS; Invitrogen). The adherent cells such as 3T3 and C2C12 cells were dissociated using Trypsin (0.25%, Invitrogen). The cells were centrifuged down and washed using buffers to be prepared in DPBS ($5\times10^5$ cells/ 15 µL/tube). Non-adherent cells such as CCRF-CEM cells or human regulatory T cells were simply washed by buffers to remove serum or other proteins which potentially interact with the PA molecules to get concentrated cell dispersion.

3.2.2. Coating with PA and Washing Steps.

The 15 µL of concentrated cell dispersion in DPBS was mixed with 10 µL of PA solution in 500 µL-tube at RT. Unless otherwise noted, the incubation time for backbone PAs and VCAMb PA is 5 minutes and 1 minute, respectively. After incubation the cell and PA mixture was transferred to a 15 mL-conical tube with 2 mL of DPBS and centrifuged down by 1,000 g for 10 minutes. The supernatant was aspirated leaving 300 µL of buffers with the cell pellet. For backbone PA, the washing step was repeated for 3 times. For further characterizations, the pellets were dissociated in 100 µL DPBS.

3.3. Characterizations on Cells.

3.3.1 Confocal Laser Scanning Microscopy.

All cells were stained by Calcein AM (Life Technologies) and Hoechst 33342 (Life Technologies) according to manufacturer's instructions for imaging and the flow cytometry analysis. For confocal fluorescence imaging and imaging with z-stacks, Nikon X1 Spinning Disk Confocal microscope in Center for Advanced Microscopy/Nikon Imaging Center (CAM), Northwestern University was utilized. For 3D reconstruction of z-stacks of confocal images, IMARIS software (Oxford Instruments) in the same center was utilized.

3.3.2. The Flow Cytometry Analysis for Coating Process Characterization.

In order to quantify the coating efficiency, mean fluorescence intensity (MFI) and the viability of the cells, LSR Fortessa and Diva software (BD Biosciences) was utilized. The coating efficiency was obtained from calculating the number of TAMRA+ cells divided by the total number of cells (Hoechst+ cells). The MFI value was obtained from living cells. The viability was calculated by dividing the number of Calcein-AM+ (living cells) by the total number of cells.

3.3.3. Phenotype Assessment of Human Treg Cells.

3.3.3.1. Flow Cytometry Analysis.

Flow cytometry was performed to monitor some of the specific Treg surface markers in nanofiber coated and non-coated Treg cells using panel of antibodies against CD3-APCH7, CD4-APC, CD25− APC cy7 (all from Beckman-Coulter, Miami, FL). All detection was performed on a Beckman-Coulter CytoFlex flow cytometer as described[3].

3.3.3.2. Treg Suppression Assay:

The responder PBMC (R-PBMC) autologous to the GMP expanded Treg cells were stimulated with fresh allogeneic third party/irrelevant donor (I-PBMC) at a ratio of 1:1 in U-bottom 96-well plates in triplicate. To initiate the mixed lymphocyte reaction (MLR) suppression assays, Treg cells or nanofiber-coated Treg cells or irradiated R-PBMC (control) were added at different ratio between Treg and Responder as indicated. The cells were cultured for 6 days in $CO_2$ incubator at 37° C. Further, the cells were added with $^3$H-thymidine (1 uCi/well) and cultured for another 16-20 hours. Proliferation of the cells measured by the incorporation of $^3$H thymidine into the DNA of the dividing cell. The MLR inhibition was performed as described previously with following formula[4].

$$\% \text{Inhibition} = 1 - \left[\frac{\Delta \text{ CPM in presence}}{\Delta \text{ CPM in presence of } Rx \text{ controls}}\right] \times 100 (\%)$$

3.3.4. Binding Assay to VCAM-1 Coated Surface.
3.3.4.1. Preparation of VCAM-1 Coated Plates.

The coating method of VCAM-1 on 96-well tissue culture plates were introduced elsewhere[5]. Briefly, the well plates were hydrated by the washing buffer (1× PBS with 1 mM $CaCl_2$) and 2 nM $MgCl_2$) for 1 minute. After aspiration, 75 µL of VCAM-1 solution (1 µg/mL) in washing buffer was placed in each well and the plates were incubated in the incubator (37° C., 5% $CO_2$). After 1 hour incubation, the VCAM-1 solution was aspirated carefully. The well surface washed gently with the washing buffer and blocked with 1% bovine serum albumin (BSA; Sigma) dissolved in the washing buffer in the incubator. After 1-hour incubation, BSA solution was aspirated. Finally, the well surface was washed gently with the washing buffer and filled with the washing buffer until use. To prepare BSA coated wells, the wells were hydrated with washing buffer, incubated with 1% BSA solution and washed. The VCAM-1 or BSA coated plates were used freshly.

3.3.4.2. Binding Cells to the Surface.

The buffers in the protein-coated well plates were aspirated and the cells dispersion were placed. Before placing the cells into the wells, the cells should be stained with the Hoechst staining. The cells were immediately spun down using centrifuge (400 g) for 5 minutes and then the plates were gently transferred to the incubator and incubated for predesignated time.

3.3.4.3. Quantification of Binding of the Cells on the Protein Surface.

After incubation, the fluorescence intensity (FI) from Hoechst staining was quantified by Cytation3 (BioTek) in Analytical bioNanoTechnology Equipment Core (ANTEC), Simpson Querrey Institute (SQI), Northwestern University. In order to unbound or non-specifically bound cells from the surface, the wells were washed gently with warm washing buffers. For comparison, the FI was measured again. After background subtraction, the binding efficiency was calculated by dividing the FI before washing by the FI after washing (%). All experiments were performed in triplicate.

3.3.5. Scanning Electron Microscopy (SEM) on Cells.

In order to immobilize the naked hTreg cells and VCAMb PA-coated cells on the cover slips, the cover slips were coated for VCAM-1 protein. The protein coating procedure was same as aforementioned. For immobilization of the backbone PA-coated cells, due to the lack of interaction between backbone PA and VCAM-1, the cover glass was coated by poly-L-lysine (Sigma). The cells with or without PA coating were immobilized on the cover glass and fixed using 4% paraformaldehyde (PFA) for 20 minutes. They were rinsed with DPBS and dehydrated by the series of ethanol solutions with increasing concentration. Ethanol was subsequently removed by critical point drying (CPD; Tousimis Samdri-795). Dehydrated samples were mounted on stubs and coated with 12 nm of osmium (Filgen, OPC-60A).

All SEM images were taken using a Hitachi SU8030 instrument operating at an accelerating voltage of 2 kV.

4. Statistical Analysis.

All statistical analyses were performed using a one-way analysis of variance (ANOVA) with a post hoc Dunnett's test using GraphPad Prim 5 software. P values<0.05 were considered to be statistically significant. P values<0.05, <0.01, <0.001 were indicated as *, , * or #, ##, ###in the graphs, respectively. All error bars in graphs are standard errors of mean.

REFERENCES (1) Weigand, S. J.; Keane, D. T., DND-CAT's new triple area detector system for simultaneous data collection at multiple length scales. *Nucl. Instrum. Methods Phys. Res., Sect. A* 2011, 649 (1), 61-63.

(2) Toby, B. H.; Von Dreele, R. B., GSAS-II: the genesis of a modern open-source all purpose crystallography software package. *J. Appl. Crystallogr.* 2013, 46 (2), 544-549.

(3) Leventhal, J. R.; Mathew, J. M.; Salomon, D. R.; Kurian, S. M.; Friedewald, J. J.; Gallon, L.; Konieczna, I.; Tambur, A. R.; Charette, J.; Levitsky, J.; Jie, C.; Kanwar, Y. S.; Abecassis, M. M.; Miller, J., Nonchimeric HLA-Identical Renal Transplant Tolerance: Regulatory Immunophenotypic/Genomic Biomarkers. *American Journal of Transplantation* 2016, 16 (1), 221-234.

(4) Mathew, J. M.; J, H. V.; LeFever, A.; Konieczna, I.; Stratton, C.; He, J.; Huang, X.; Gallon, L.; Skaro, A.; Ansari, M. J.; Leventhal, J. R., A Phase I Clinical Trial with Ex Vivo Expanded Recipient Regulatory T cells in Living Donor Kidney Transplants. *Scientific reports* 2018, 8 (1), 7428.

(5) Strazza, M.; Azoulay-Alfaguter, I.; Pedoeem, A.; Mor, A., Static adhesion assay for the study of integrin activation in T lymphocytes. *J Vis Exp* 2014, (88).

Results and Discussion

The short peptide sequence VHPKQH (SEQ ID NO: 1) was used for presentation from PA fibers as a modified mimic of the sequence VHPKQHR (SEQ ID NO: 11) to increase the solubility at physiological pH. VHPKQHR (SEQ ID NO: 11) was developed from phage display technique[47, 48] and identified as a part of VLA-4 which is a known ligand for VCAM-14. FIG. 1A shows the procedure for coating the surface of individual cells with ECM-like self-assembled PA nanofibers. The cells were first prepared as an aqueous dispersion in Dulbecco's phosphate buffered saline (DPBS). Since the PA nanofibers with charges could interact with the proteins in the serum and form random aggregates, the cells were washed with DPBS to remove residual serum and other cellular proteins. The PA solution was prepared by dissolving PA in distilled water and thermally annealed to produce elongated stable nanofibers as described previously[49]. Finally, the cell dispersion was mixed thoroughly with the PA solution and incubated for several minutes at room temperature. Finally, the cells were thoroughly washed with repeated addition of DPBS, centrifuged, and the supernatant was discarded.

Figure 1B:
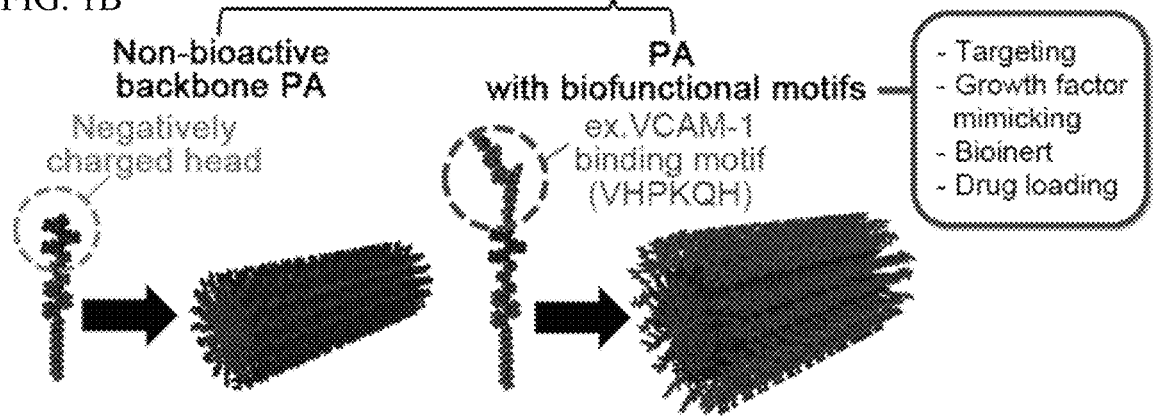
Figure 2A:
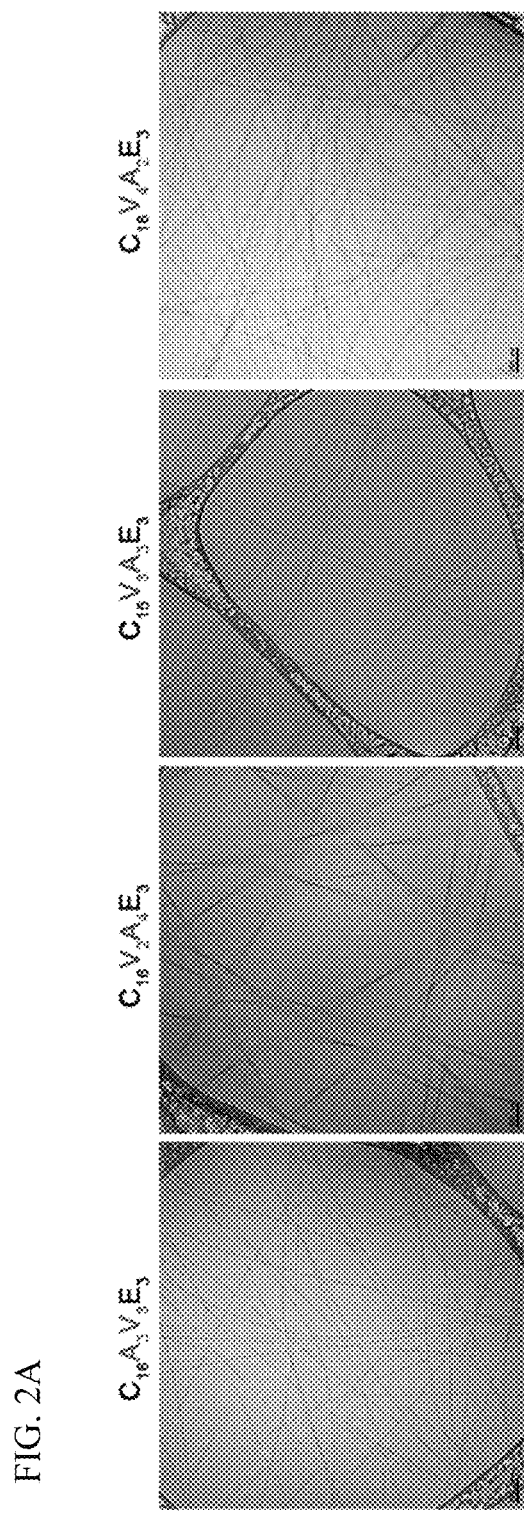
Figure 2B:
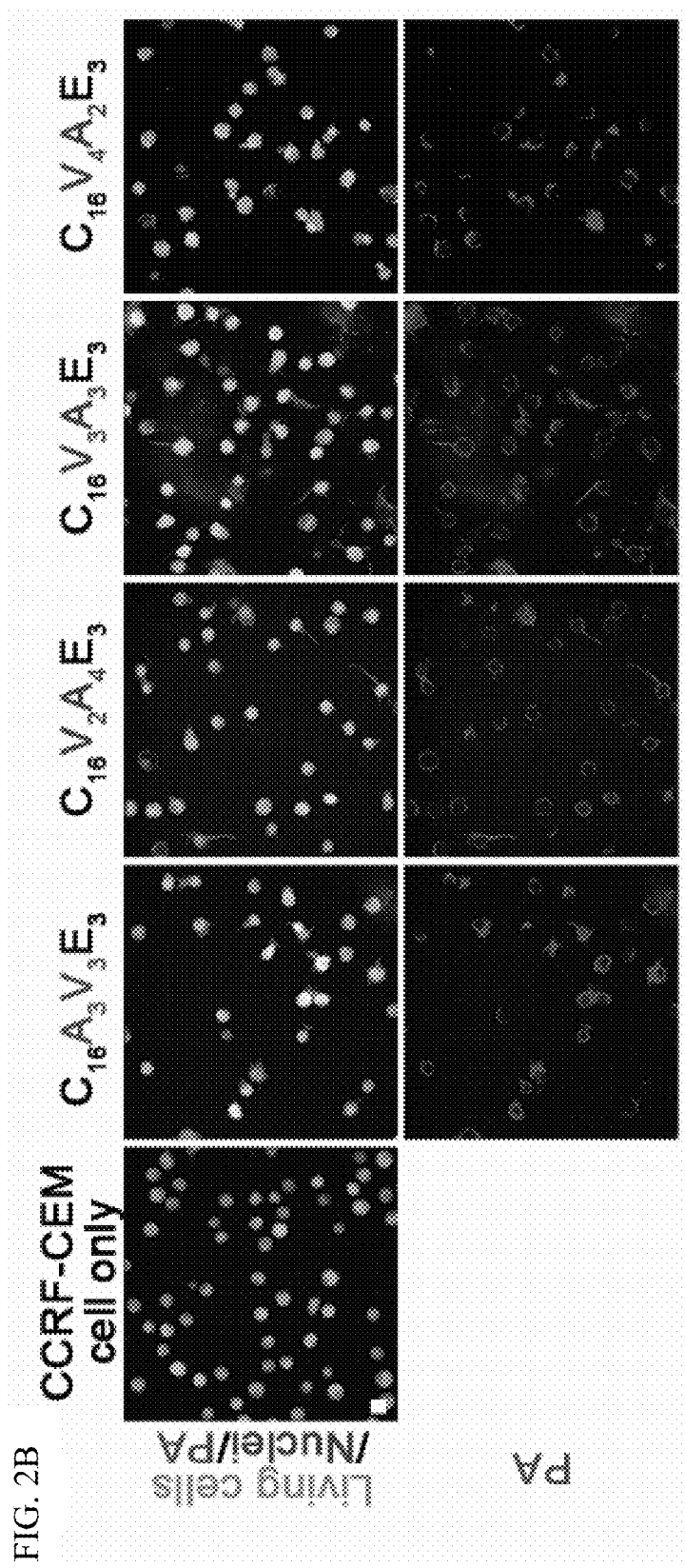
Figures 2C, 2D:
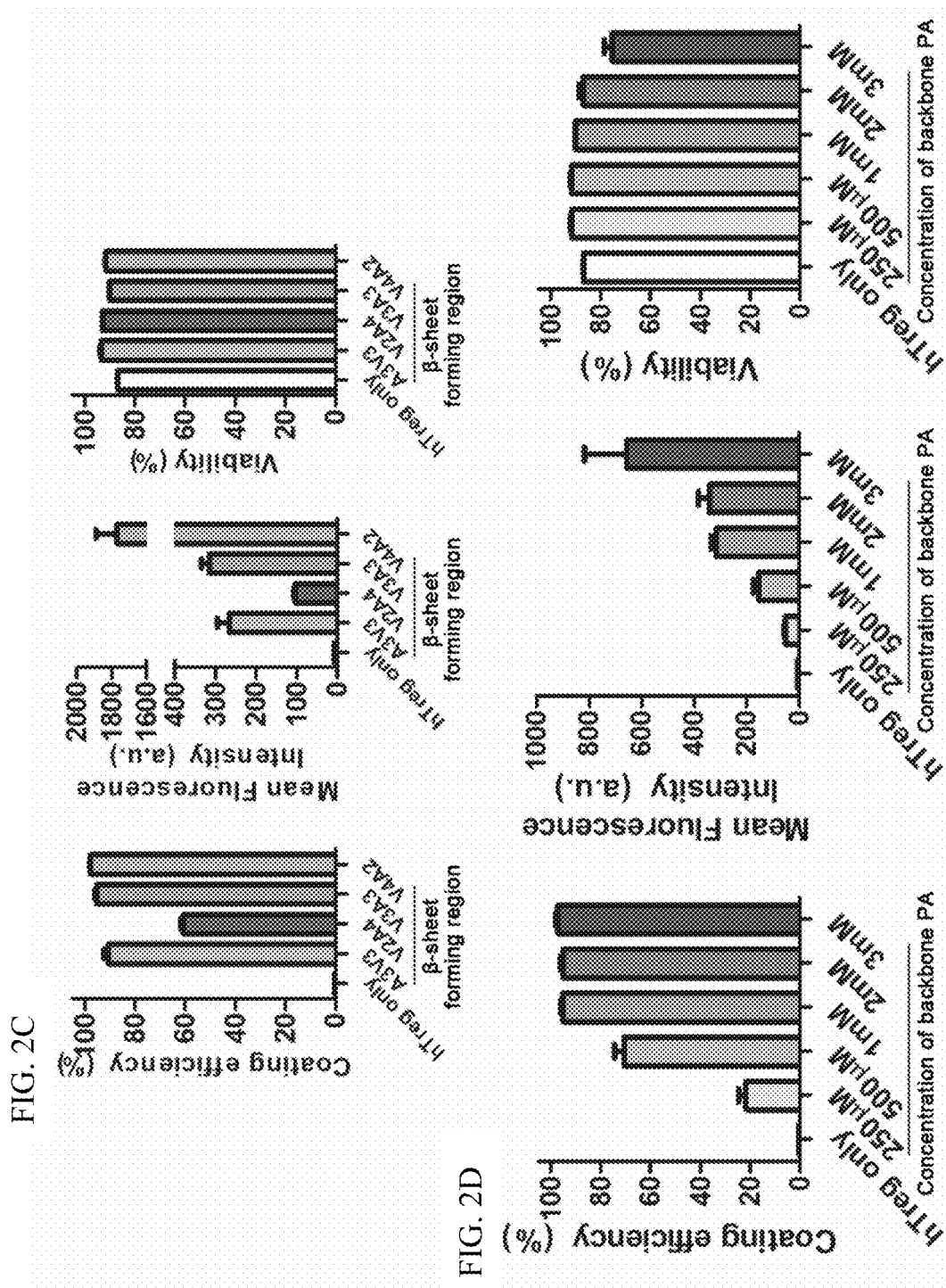

The non-bioactive backbone PA (FIG. 1B) was employed for the system development and the optimization of the coating process. In order to optimize the coating efficiency, several backbone candidates were synthesized with different β-sheet regions, namely $A_3V_3$ (SEQ ID NO: 7), $V_2A_4$ (SEQ ID NO: 8), $V_3A_3$ (SEQ ID NO: 6), $V_4A_2$(SEQ ID NO: 9), which were sandwiched by hydrophobic palmitoyl tail ($C_{16}$)

and a negatively charged glutamic acid head ($E_3$) (FIG. 2). These candidates were screened for nanofiber formation and biocompatibility[23]. For fluorescence imaging and flow cytometry analysis, nanofibers were doped with 1 mol % of PA molecules fluorescently labelled with carboxytetramethylrhodamine (TAMRA)[50] and utilized to coat the model cells (CCRF-CEM; T-cell like cell lines). All candidates formed long and smooth nanofibers after annealing and were able to coat the cell surface, as confirmed by cryogenic transmission electron microscopy (cryo-TEM) and confocal microscopy. The whole cell surface could be wrapped by the nanofibers, except for $C_{16}$-$V_4A_2E_3$ (SEQ ID NO: 12) fibers, which only could partially cover the cell surface. Coating success was characterized by the mean fluorescence intensity (MFI) from TAMRA in the nanofiber coating. Except for $C_{16}$-$V_2A_4E_3$ (SEQ ID NO: 13) PA, the other E3-based PAs coated the cell surface with over 90% of efficiency and similar cytotoxicity for all sequences tested (FIG. 2C). Based on the fluorescence results, $C_{16}$-$V_3A_3E_3$(SEQ ID NO: 5) PA nanofibers were used in the following experiments.

Figure 1C:
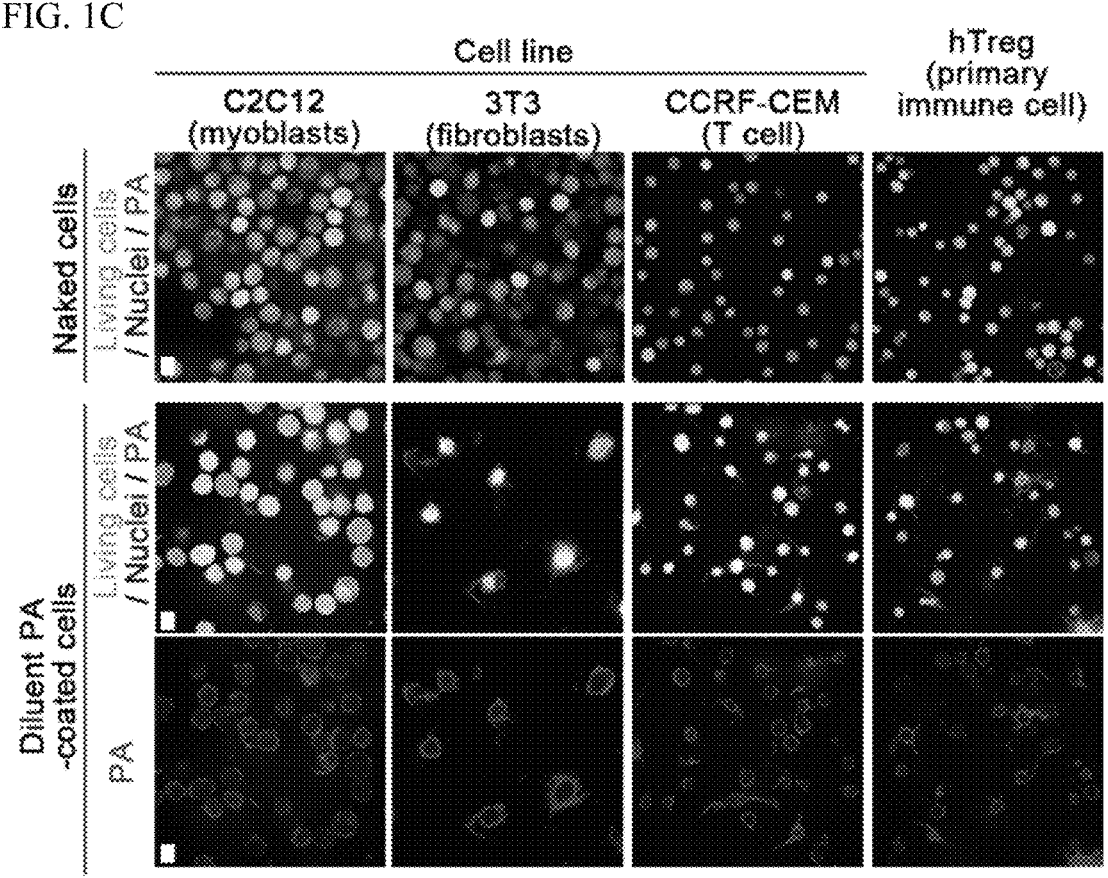
Figure 1D:
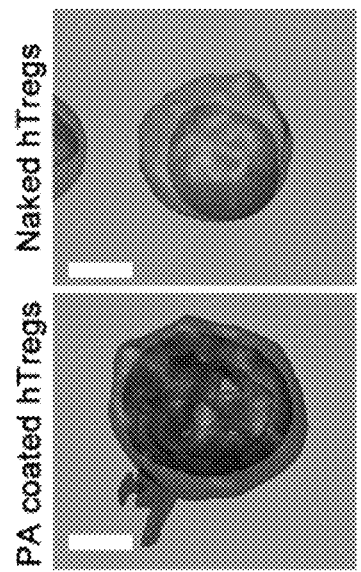
Figure 1E:
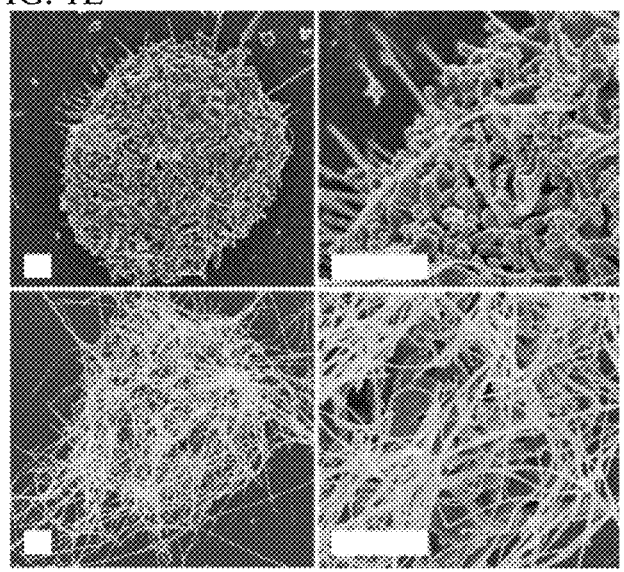
Figure 7A:
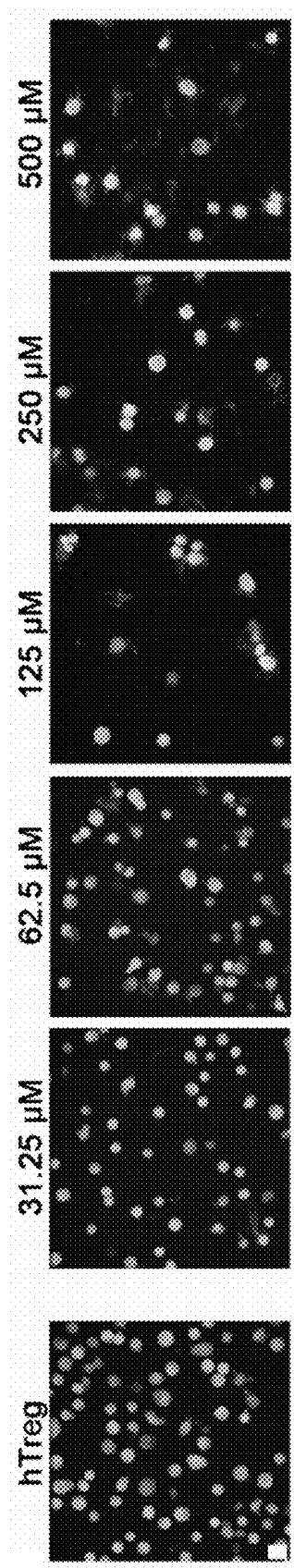
Figure 7B:
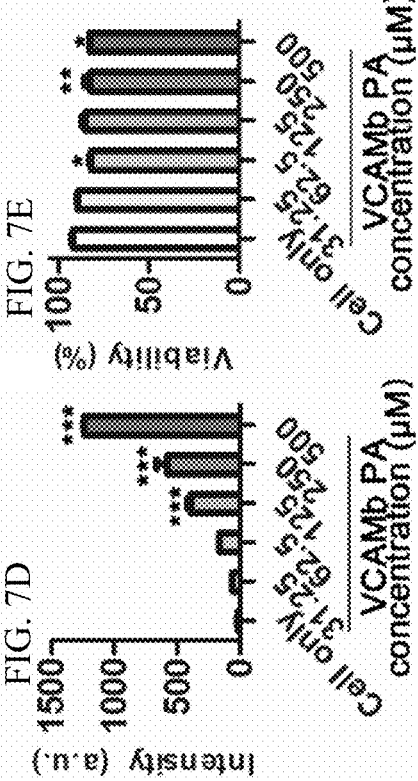
Figure 7C:
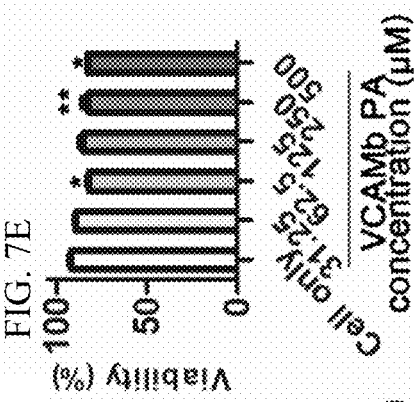
Figure 7D:
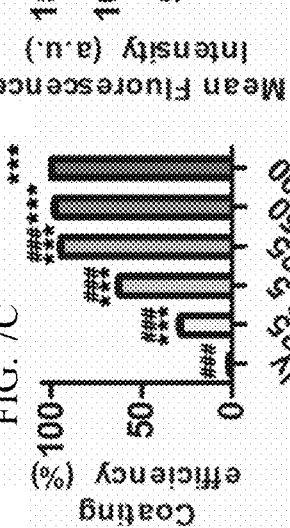
Figure 7E:
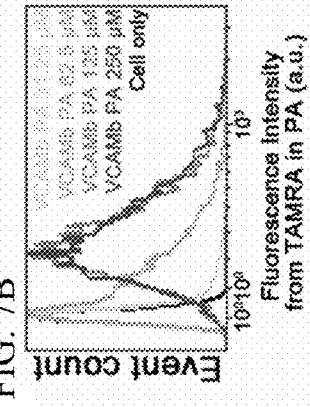
Figures 7F, 7G, 7H:
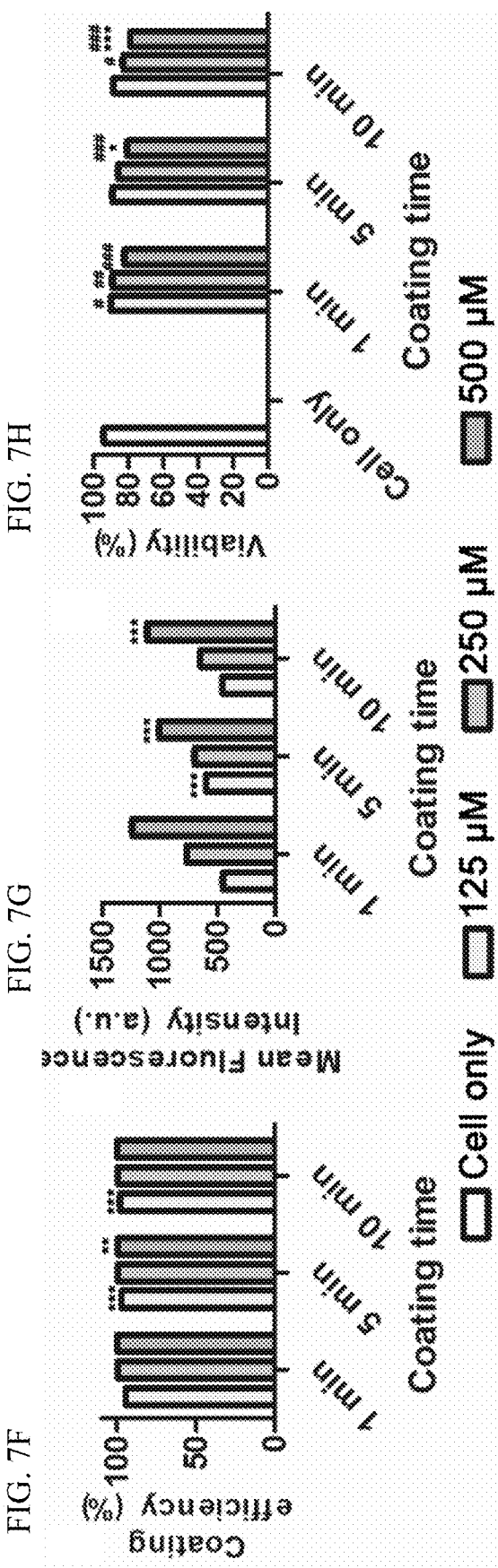
Figure 8:
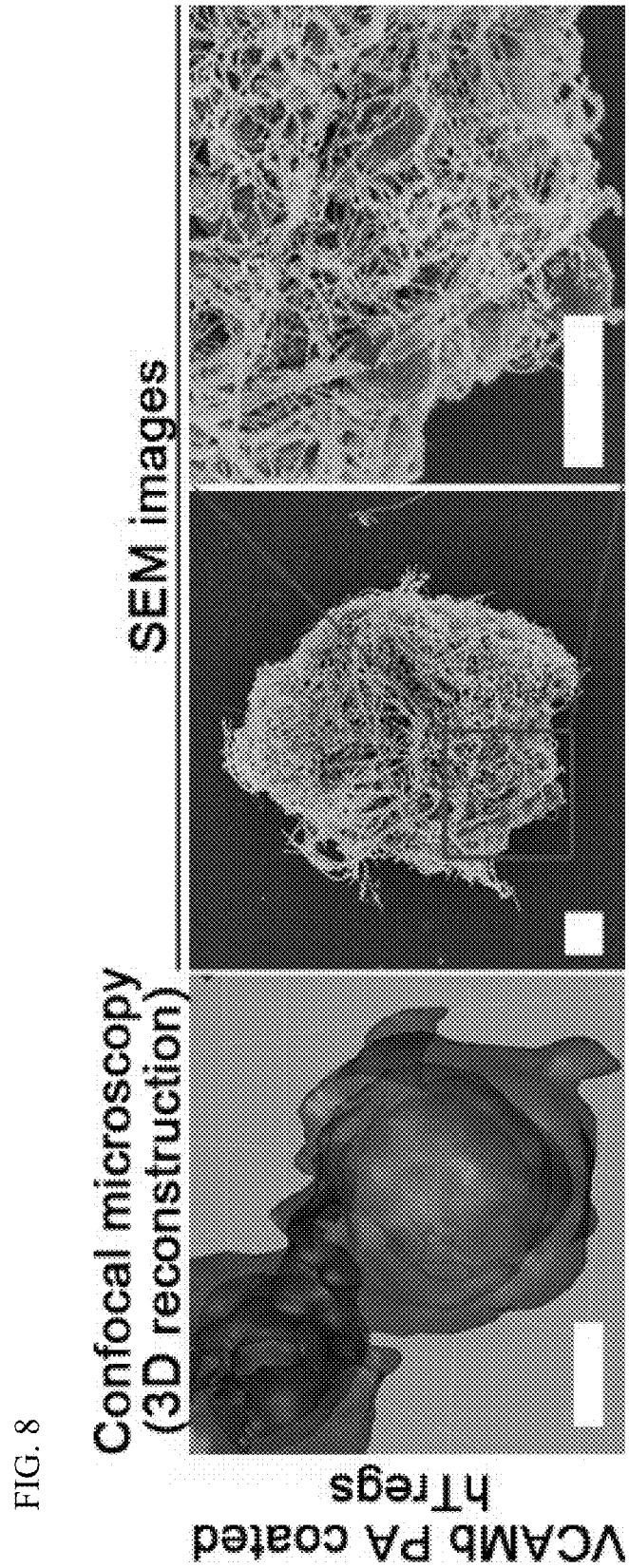

Fluorescence images from confocal laser microscopy show cell from various lineages (myoblast, fibroblast and T lymphocyte-like) and primary cells (human regulatory T cells; hTregs) coated with the backbone PA nanofiber (FIG. 1C). The PA coating appear as red rings, such as in the bottom panels of the TAMRA channel alone. Different concentrations of the backbone PA nanofibers were utilized to coat the cell lines including CCRF-CEM (FIG. 2D) and human Tregs (FIG. 3) to optimize the experimental parameters. Three-dimensional reconstructions of the confocal images show that the cell surface was wrapped by the nanofibers with or without the targeting peptide in a 3-dimensional manner (FIG. 1D).

The non-bioactive[29, 51] backbone PA was terminated with three glutamic acids at the surface of self-assembled nanofibers; thus, the nanofibers had an overall negative charge. Interaction between the PA nanofibers and the cell surface occurred in a variety of cell lineages. These observations lead to a distinctive difference between the method presented here and previously reported cell surface decoration or encapsulation methods since the coating described herein is not driven by electrostatic, antigen-antibody, or receptor-ligand interactions. SEM imaging was also performed on the PA nanofiber-coated cells to characterize the interface between PA nanofibers and the cell surface. SEM analysis demonstrated nanofibers were able to entangle with the microvilli on the cell surface during the coating process (FIG. 1E). The thinner nanofibers were entangled with the thicker features from the cell surface (indicated by red arrows). For comparison between the behavior of short and long PA structures in the coating process, the long PA nanofibers were mechanically shortened by sonication after annealing and utilized for cell surface coating. The confocal image from the C2C12 cells coated by the shorter PA structures (bath sonicated PA nanofibers) shows the fluorescence intensity from the PA nanofibers decreased and the smaller PA structures infiltrated into the cytosol (FIG. 4). Based on these observations, it was thought that the coating was achieved as a result of the physical entanglement of long PA nanofibers between the features on the cell surface, including the microvilli.

VCAM-1 targeting peptide (VHPKQH (SEQ ID NO: 1)) was added to the backbone PA forming VCAM-1 binding PA (also referred to herein as VCAM-1 targeting PA or VCAMb PA; $C_{16}$-$V_3A_3E_3$GSGVHPKQH (SEQ ID NO: 14). The targeting peptide was linked to the backbone PA with tripeptide linker, GSG, to ensure the bioavailability of the targeting peptide.[52, 53] To avoid potential issues with low solubility of the PA with the full VCAM-1 targeting peptide sequence VHPKQHR (SEQ ID NO: 11) ($C_{16}$-$V_3A_3E_3$GSGVHPKQHR (SEQ ID NO: 15)) at physiological pH, the sequence was modified to omit the arginine (R) at the C-terminus (VHPKQH (SEQ ID NO: 1)). A PA with a scrambled sequence VHPKQH (SEQ ID NO: 16) (VCAMb-scr; $C_{16}$-$V_3A_3E_3$GSGQHPHVK (SEQ ID NO: 17)) was used as a control to confirm the specificity of the sequence to bind to VCAM-1 protein[54]. Cryo-TEM (FIG. 5A) confirmed that the backbone PA and VCAMb PA form long thin twisted ribbons; however, VCAMb-scr PA formed relatively short fibers closely packed to each other. The microscopy results on backbone and VCAMb PA agree with small-angle X-ray scattering (SAXS) analysis (FIG. 5B). It shows, for both backbone and VCAMb PA, the slope of −2 in the Guinier region, which indicates a flat structure. Measurements of circular dichroism (CD) were carried out in order to assess the hydrogen bonding within the PA nanofibers (FIG. 5C). CD spectra of backbone and VCAMb PA nanofibers showed the β-sheet signals as indicated by the positive and negative bands at approximately 200 and 220 nm[55], respectively. Zeta potential measurement was performed on the PA nanofibers to assess the effect of net charge of the nanofibers on the coating behavior (FIG. 5D). The measured zeta potential of the backbone PA and VCAMb PA were −37.1±2.425 mV, and 21.4±3.703 mV, respectively. Due to the extra positive charges of VCAMb targeting peptide, the net charge of VCAMb PA was positive. VCAMb-scr PA also showed positive zeta potential (6.313±0.8632 mV), which is lower than that of VCAMb PA. This difference in charge could explain the difference between structures of VCAMb and VCAMb-scr PA nanofibers.

To assess the binding capability of VCAMb PA to VCAM-1 protein, biolayer interferometry (BLI, FIG. 5E) was employed. Except for VCAMb PA, the backbone PA and VCAMb-scr PA did not show the association peaks at all concentrations of PA investigated (0.1 mM-100 nM, FIG. 6), which indicate there is negligible binding between those PA and the target VCAM-1 protein. On the other hand, the VCAMb PA demonstrated clear association between VCAM-1 protein and VCAMb PA and its dissociation constant ($K_D$) was measured to be 279.5 nM. Compared to the $K_D$ value of VCAMb targeting peptide (VHPKQHR (SEQ ID NO: 11)) measured from another group using surface plasmon resonance (SPR)[56], $K_D$=39.60±1.78 nM, the measured $K_D$ value was higher which indicates slightly weaker binding than the free floating peptide molecules. It can be explained possibly due to the steric hinderance from the nanostructures and also the slight modification of the epitope through the removal of arginine.

The feasibility of using this coating approach was next evaluated with VCAM-1 PA on hTreg cells (FIG. 7). PA nanofibers could coat the cell at significantly lower concentrations than the backbone PA (FIG. 7A), presumably due to positive charge of VCAMb PA. The quality of the coating was evaluated as a function of coating efficiency, MR, and the viability was evaluated using TAMRA-labeled PA nanofibers and cells stained with Calcein AM (living cell staining) and Hoechst 33432 (nuclei staining). The details of methods used to calculate these parameters are described in the Experimental section. Human Treg cells were successfully coated (≥95% coating efficiency) by VCAMb PA nanofibers in the range of 125-500 μM. With lower concentrations, some cells were coated with PA nanofibers on parts of their surface, but the majority of the cells were completely uncoated (FIG. 7A). These results are consistent with the fluorescence intensity histogram where based on coating efficiency and the peak shifting, and it was therefore concluded that the minimal concentration of stable VCAM-1 coating is 125 µM (FIG. 7B). The viability of PA coated hTregs has a weak tendency to decrease as the concentration of VCAMb PA increases. The viability for the cells with 125, 250, and 500 µM VCAMb PA was 85.23±5.3%, 82.62±7.45%, and 82.53±0.61%, respectively. Those values were 92.6%, 89.7% and 89.6% compared to the viability of negative control (non-treated hTreg cells; 92.07±2.45%). SEM shows VCAMb nanofibers were attached to the cell surface presumably due to the electrostatic interaction, in addition to the entanglement with the microvilli on the cell surface (FIG. 8). The effect of positive charges on the cell viability could be minimized to use minimal concentration of the VCAMb PA. The analysis was performed using different coating times ranging from 1 to 10 minutes at room temperature (FIG. 7F-H). There was little effect on coating efficiency with varied coating time, MF and viability except at high concentrations (500 µM) of the VCAMb PA. The cells were coated within 1 minute by VCAMb PA nanofibers with ~100% (≥94.5%). At high concentration, however, the viability slightly decreased as the coating time increased (p<0.001). Coassembly of VCAMb PA with the non-bioactive backbone PA to investigate the morphology of the fibers, and coating behavior as a function of molar ratios (FIG. 9). As shown by cryo-TEM, coassemblies with 30 to 70 mol % VCAMb PA showed aggregates of nanostructures rather than long smooth fibers, likely due to electrostatic attractions between the opposite surface charges. The ζ-potential of the coassembled structures was nearly zero (≤20 mV), indicating structures with very little net surface charge. By CD analysis the backbone, 100% VCAMb PA and co-assembled PAs still demonstrate β-sheet signals. However, with VCAMb PA, particularly in the case of 30 and 50 mol %, the β-sheet signals were severely reduced, which is consistent with the short fiber aggregates observed by TEM. Utilized in the coating system, however, most coassembled nanofibers (10-70 mol % VCAMb PA) aggregated together instead of coating the cell surfaces.

Figures 10A, 10B, 10C:
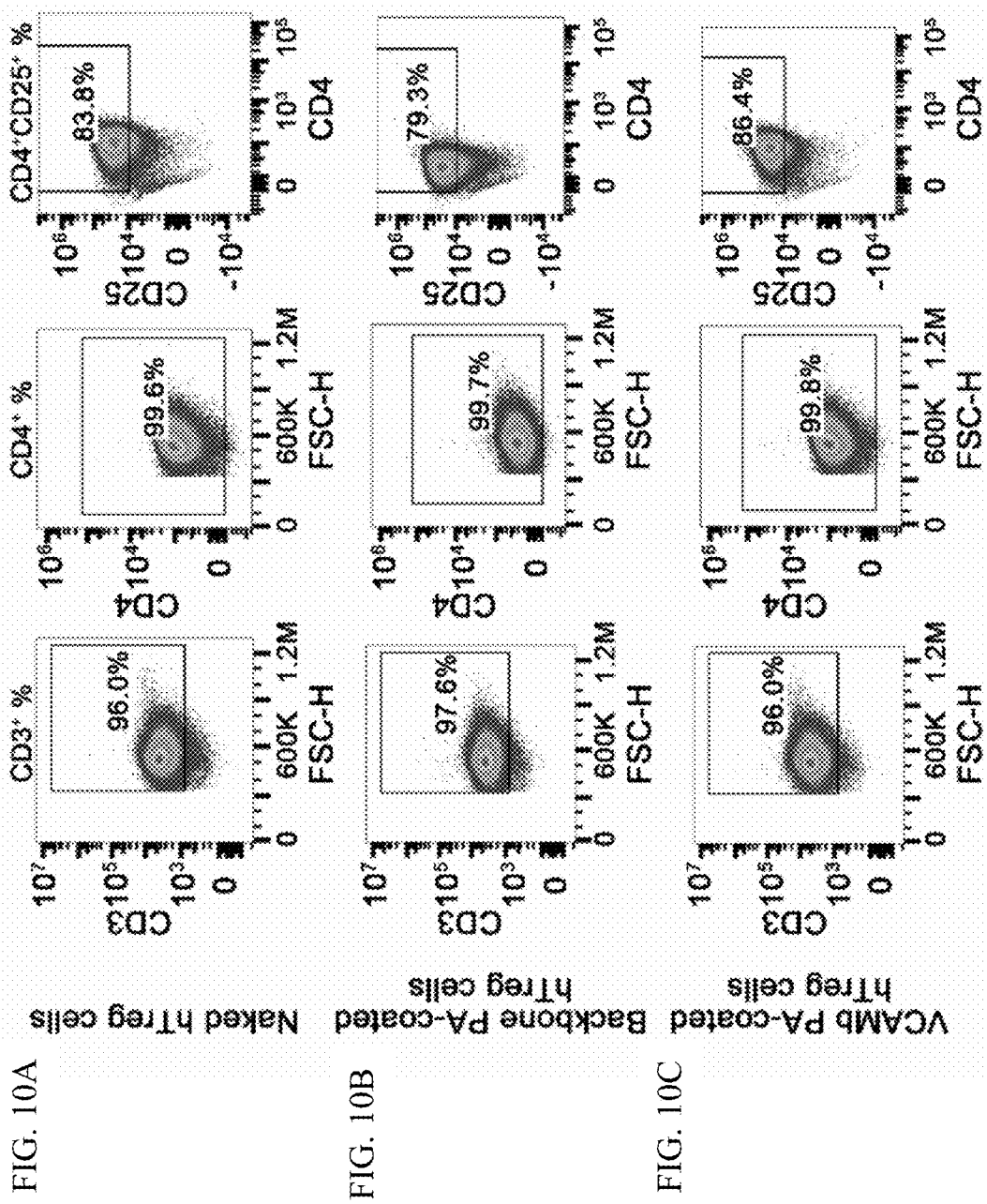
Figure 11:
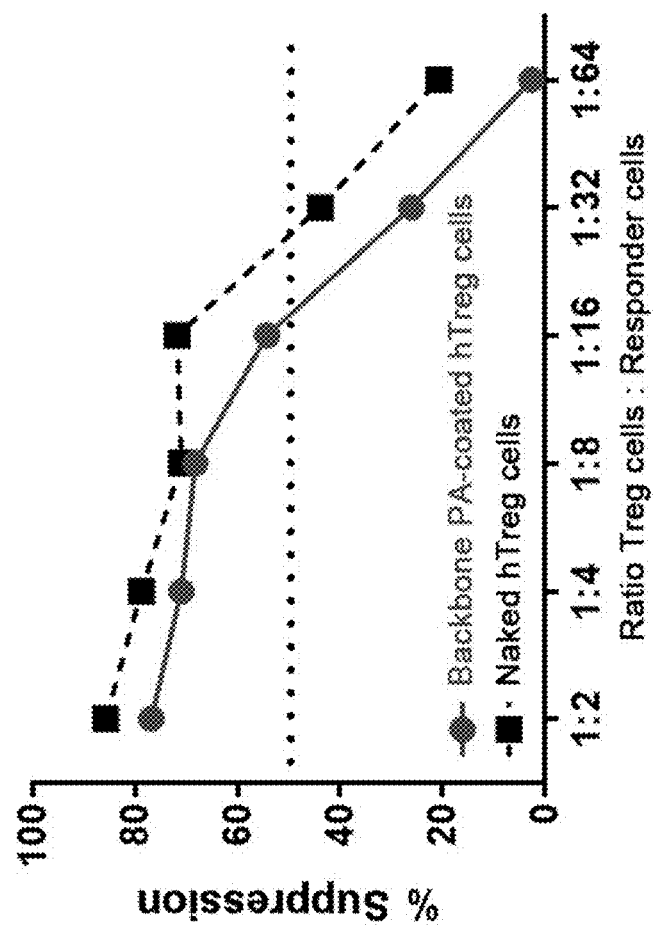
Figure 12:
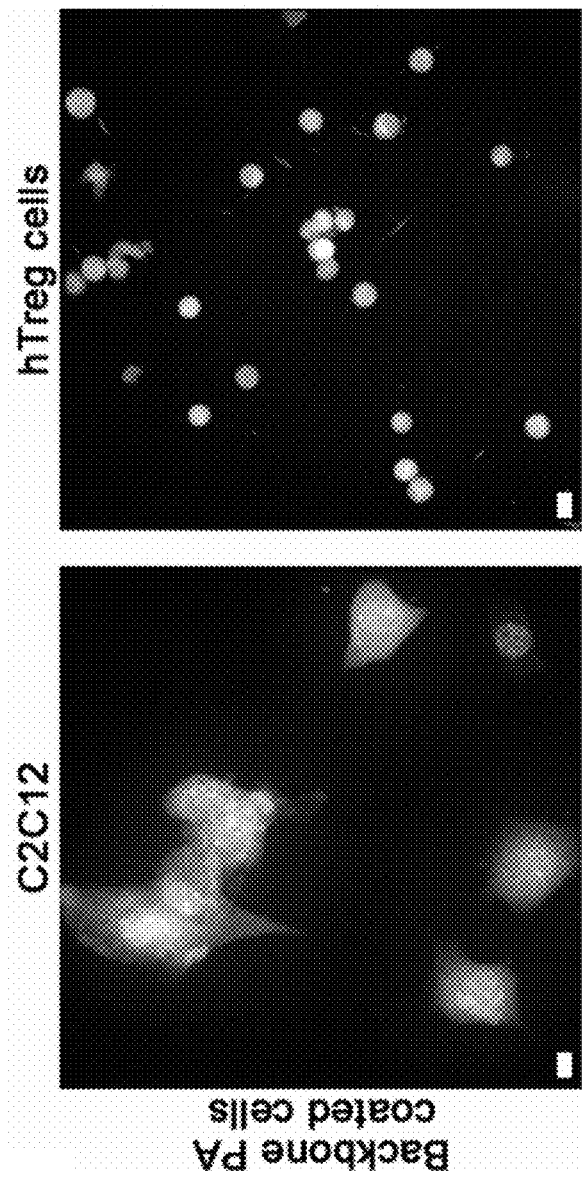

The characteristic surface markers of PA-coated human Treg cells were characterized in order to confirm that the PA coating on the outside of the cells did not negatively affect the cellular phenotypes (FIG. 10). The CD4 and CD25[36] were utilized as representative surface markers of regulatory T cells in this study and the percentages of the positive cells for those surface markers were compared. In the case of uncoated hTreg cells, 83.8% of the cells were positive for both CD4+ and CD25+. For the backbone and VCAMb PA nanofiber-coated hTreg cells, the percentages of the positive cells for both surface markers were not significantly different from the negative control (79.3 and 86.4%, respectively). Since the interaction between the PA coatings stick to the cells via physical entanglement-derived rather than chemical- or receptor-mediated interactions, the surface markers were not affected. In order to confirm the immune suppressive function of the cells was retained in the presence of the coating, mixed lymphocyte reaction (MLR) suppression assays were performed (FIG. 11). There was no statistical difference between the MLR inhibition profiles using naked hTreg and backbone PA nanofibers-coated hTreg cells. VCAMb-scr PA was not utilized for these experiments, the majority of the cells were not coated by the fibers, since the fibers formed their own aggregates in the physiological buffers (FIG. 9). These findings on surface marker characterization and MLR tests indicate that the coating procedures and the physical presence of PA nanofibers with or without the functional peptides on the cell surface did not significantly affect the phenotype and the function of the coated cells, which is an essential feature for practical future cell therapies. Furthermore, the coating on the outside of the cells were transient, which is suitable for targeted delivery of the autologous cells to lesions (FIG. 12). Since the circulation time required for targeted delivery followed by systemic injection such as intravascular injection or intraarterial injection is approximately 2 hours in mice[5], the transient PA nanofiber coating on the cell surface will be internalized by the therapeutic cells and will be broken down, thus, it will have little effect on the coated cells and adjacent cells in cellular environment in target lesions for a long time. It is presumed that the MLR test, which took seven days, was not affected by the transient coating. After overnight culture, the PA coating on C2C12 and hTreg cells was internalized into the cytosol. In confocal images, the red dots and short fibers inside of the cells were observed.

Figures 3A, 3B, 3C:
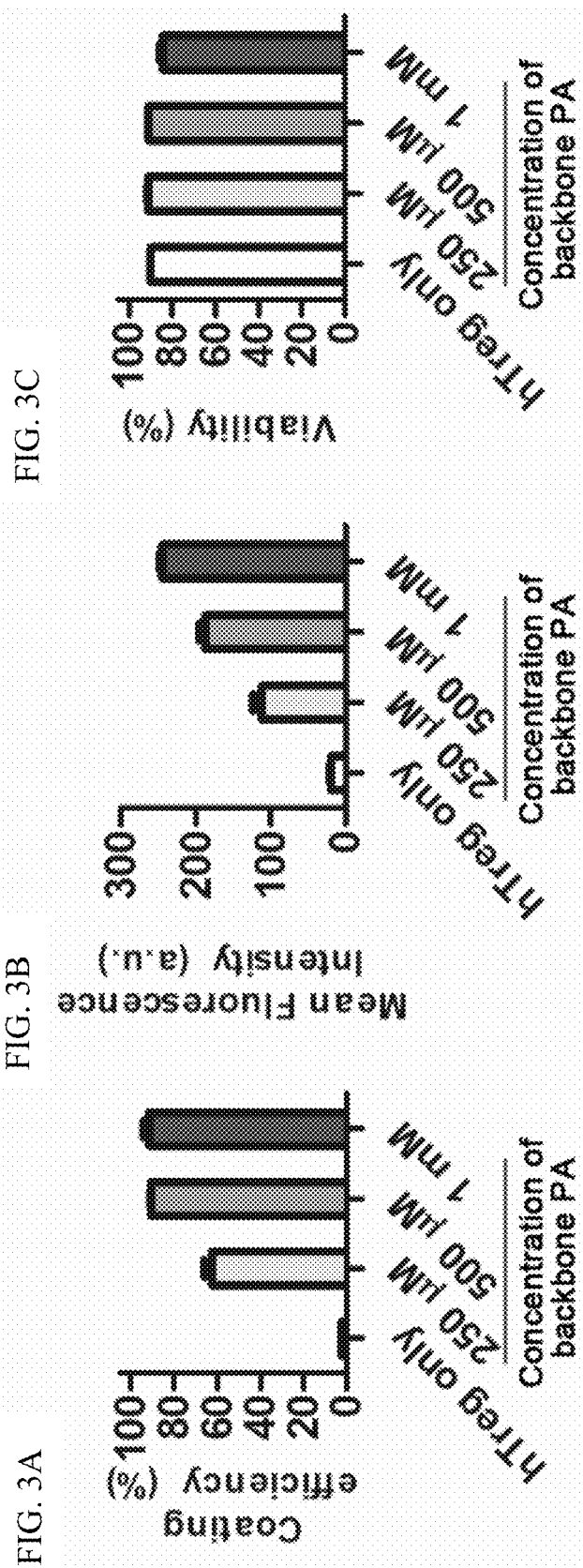
Figure 3D:
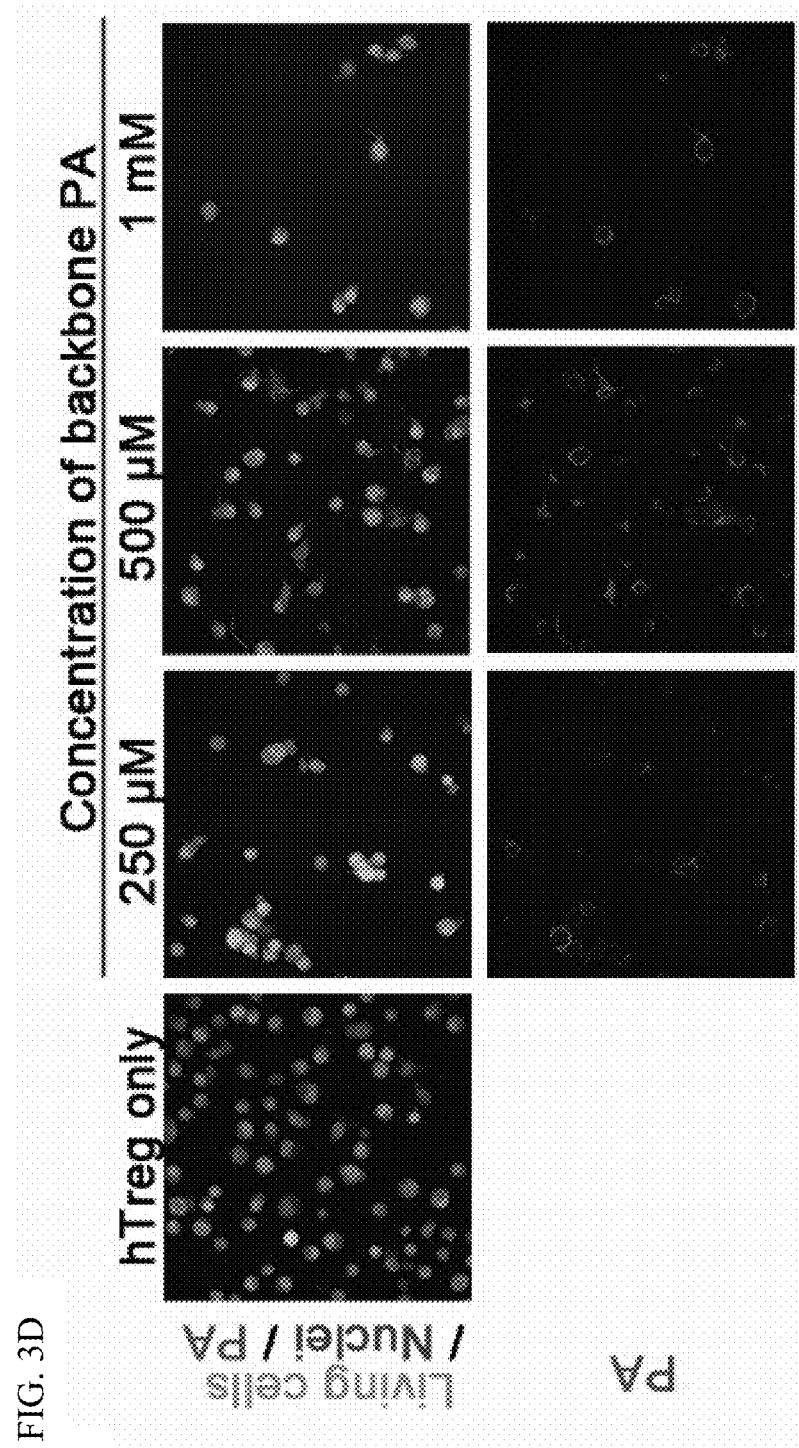
Figure 4:
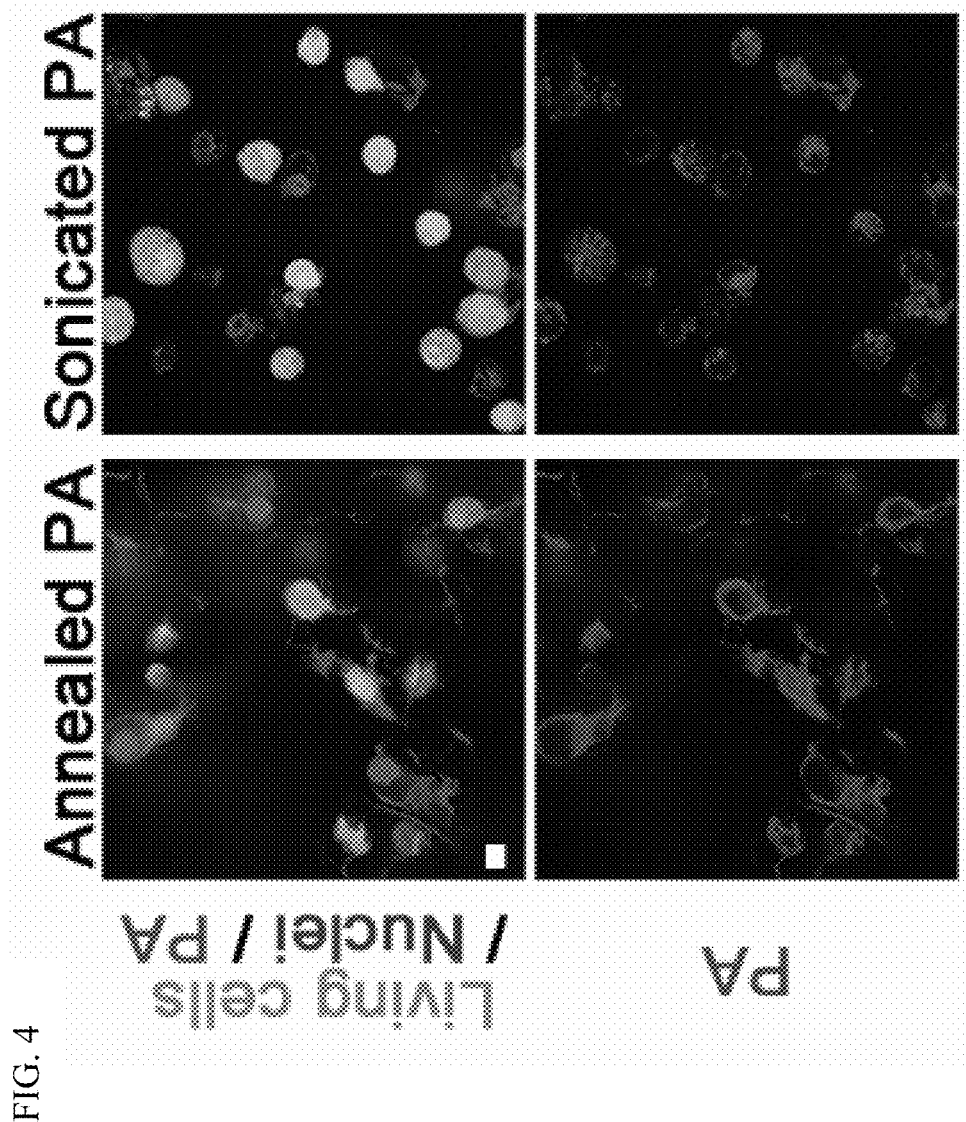
Figure 5A:
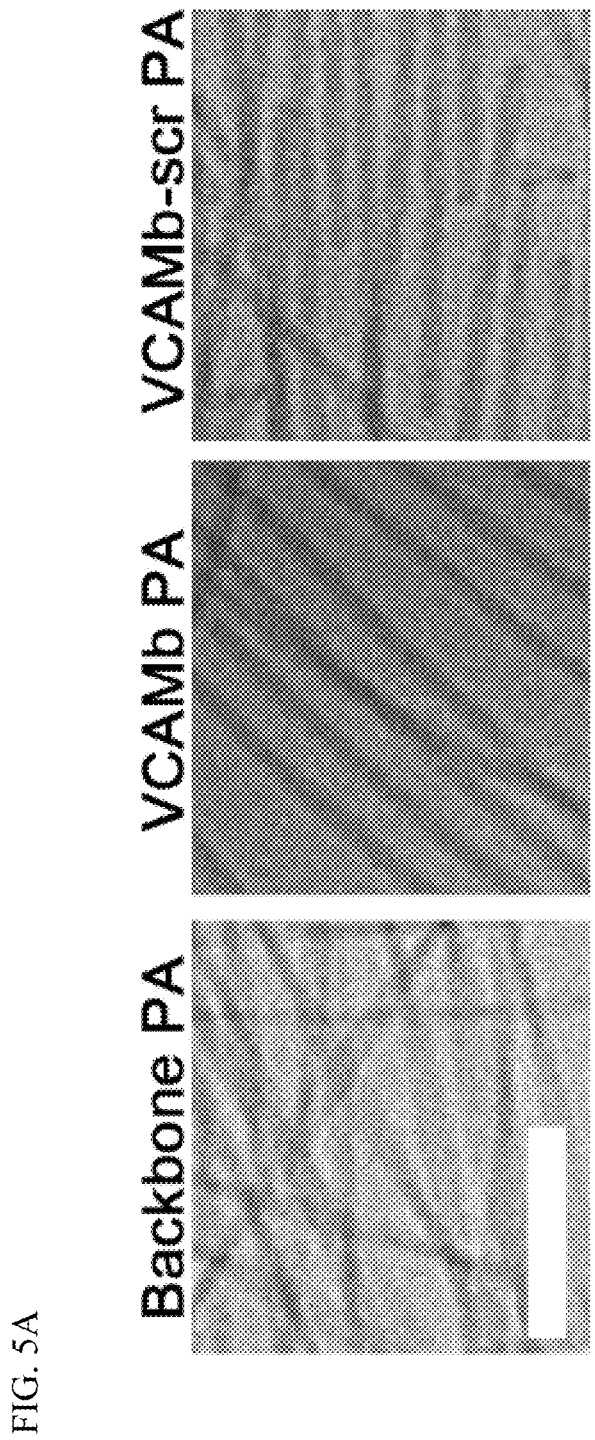
Figure 5B:
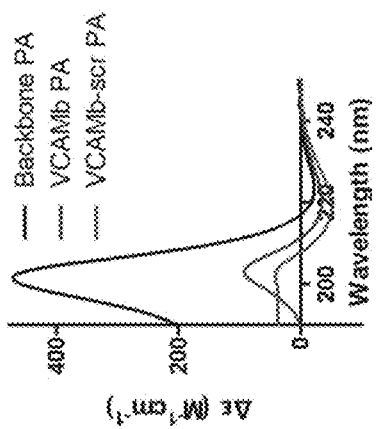
Figure 5C:
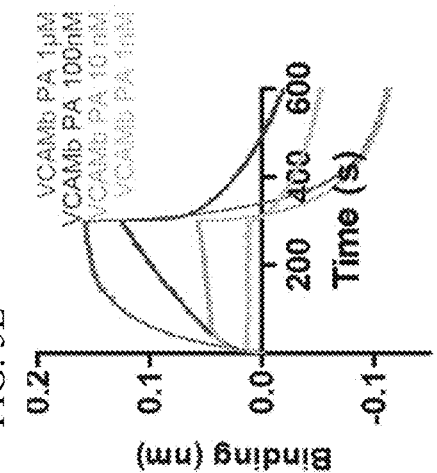
Figure 5D:
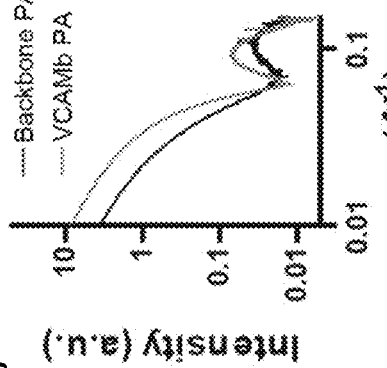
Figure 5E:
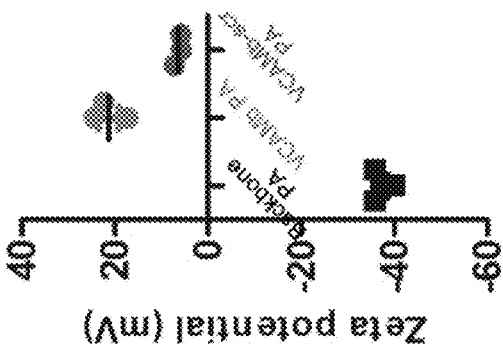
Figure 6:
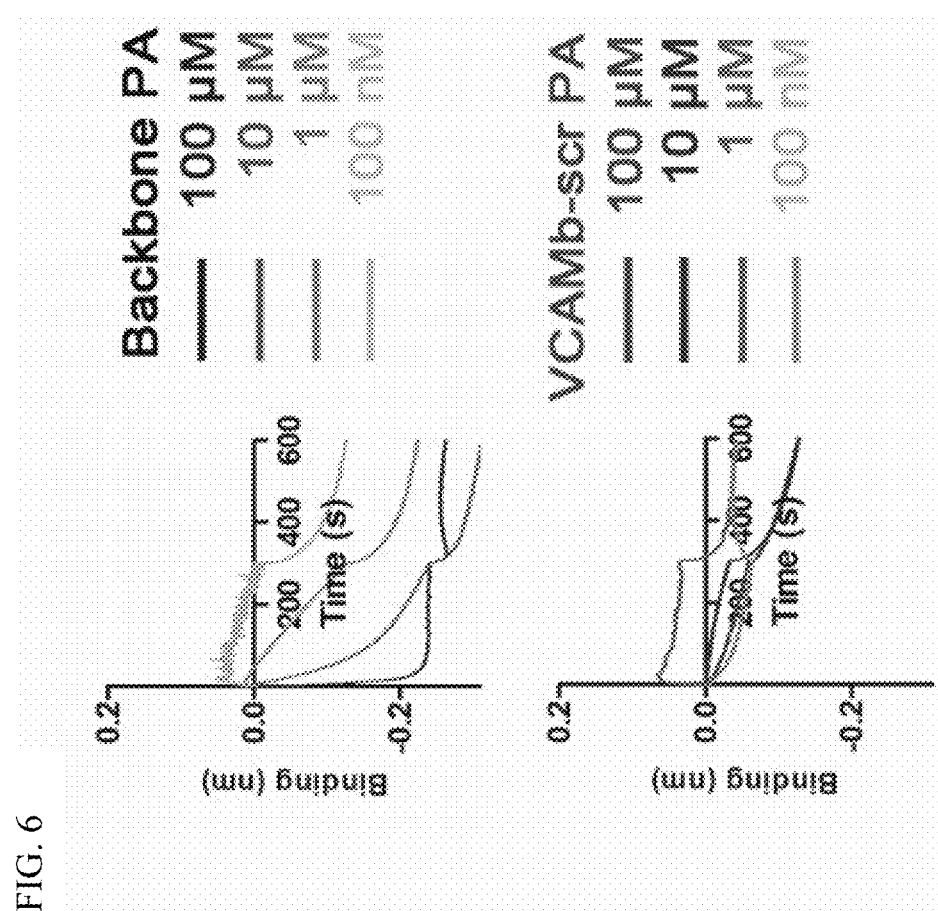
Figure 13A:
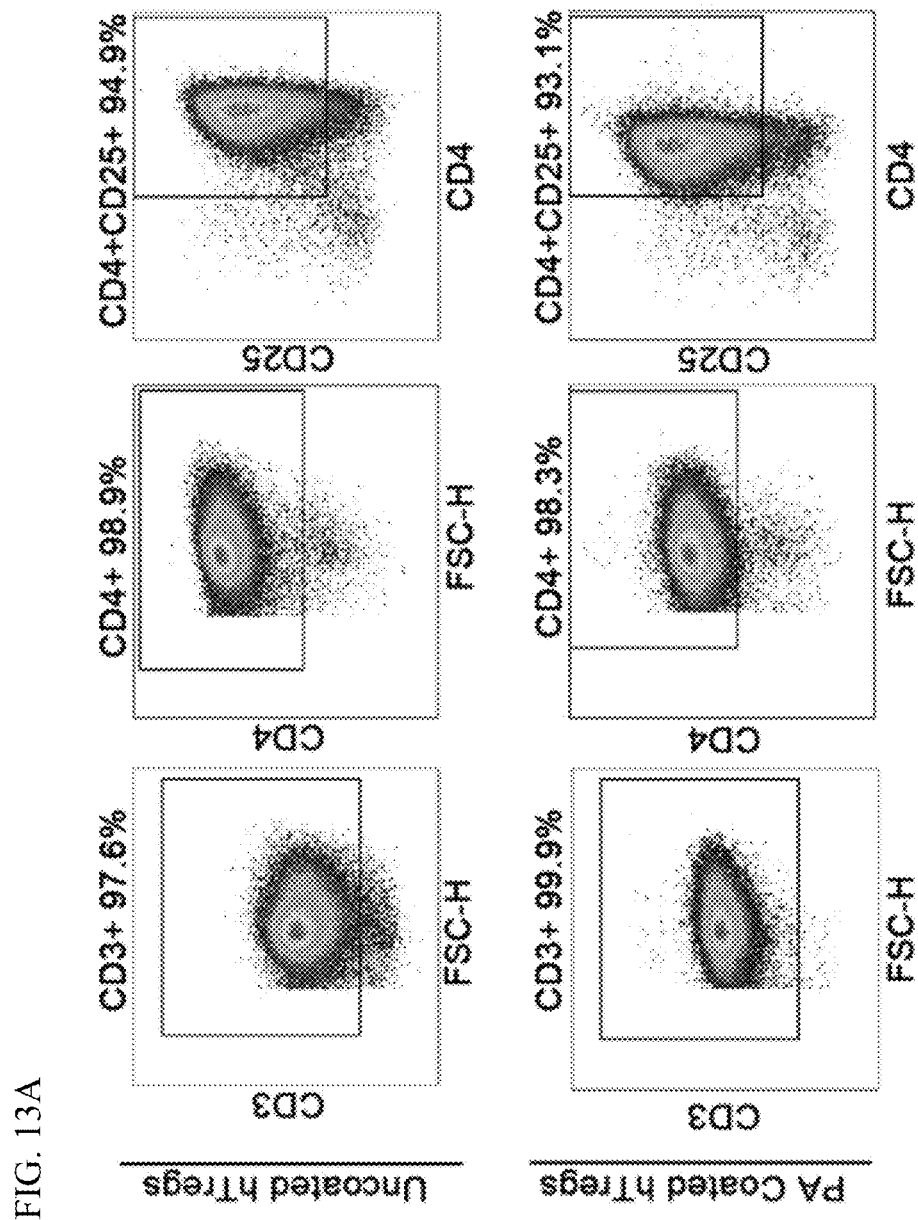
(FIG. 13A) Flow cytometry density plot showing phenotyping marker expression of CD3+, CD4+ and CD25+ in uncoated and PA coated ($C_{16}V_3A_3E_3$) hTregs.
Figure 13B:
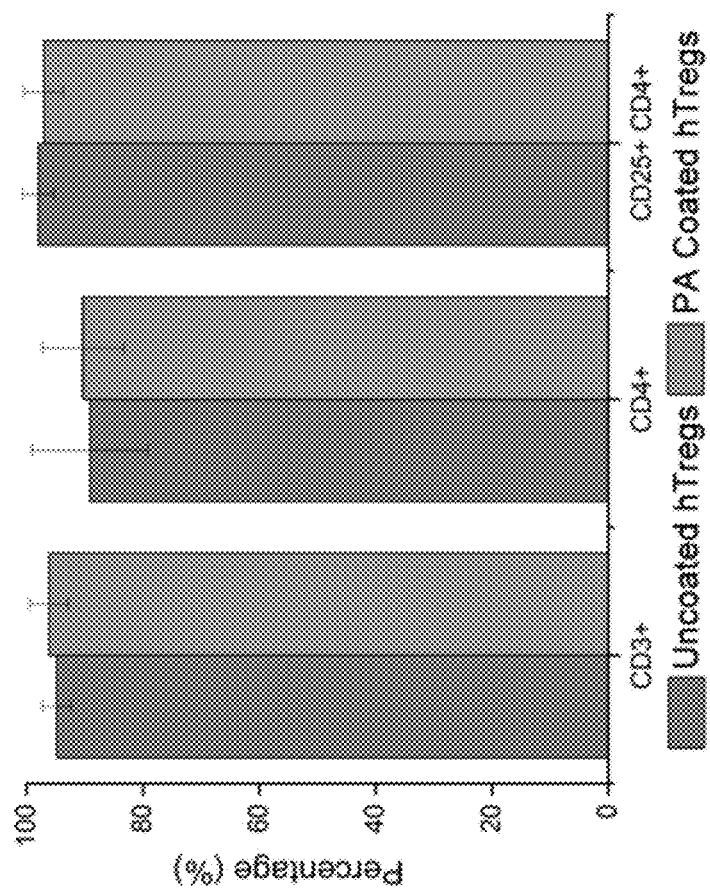
(FIG. 13B) Comparison of marker expression of CD3+, CD4+ and CD25+ in uncoated and PA coated ($C_{16}$-$V_3A_3E_3$(SEQ ID NO: 5)) (n=3).
Figure 13C:
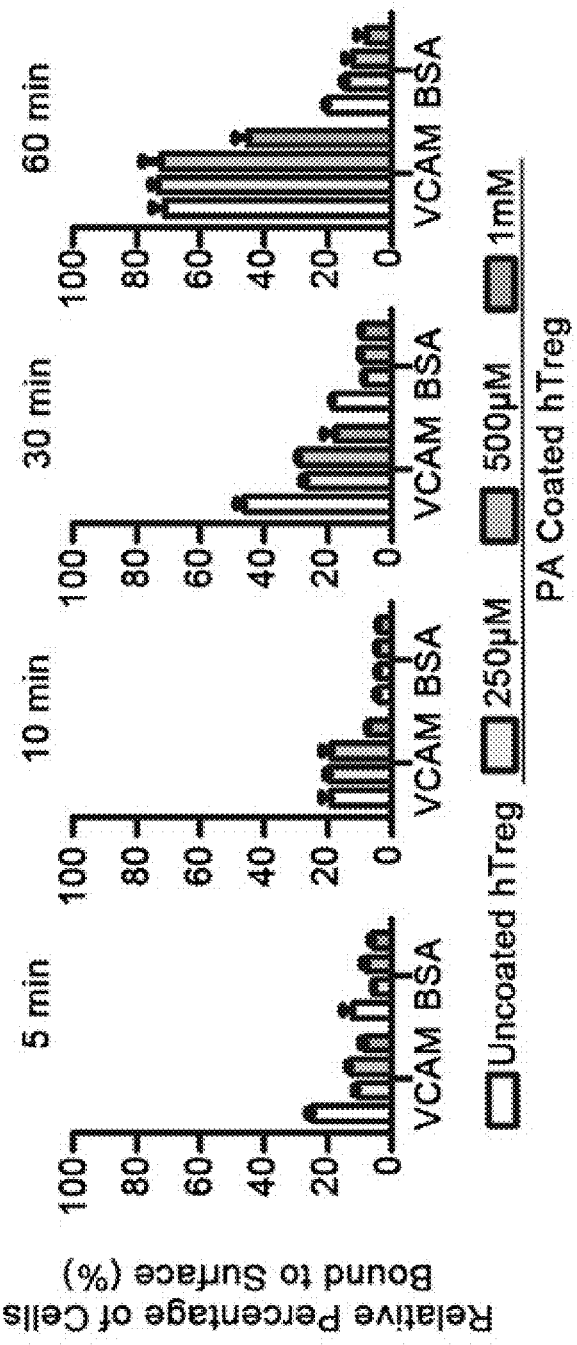
(FIG. 13C) Measurement of the relative binding of uncoated and PA coated($C_{16}$-$V_3A_3E_3$ (SEQ ID NO: 5)) hTregs to a VCAM-1 protein.
Figure 13D:
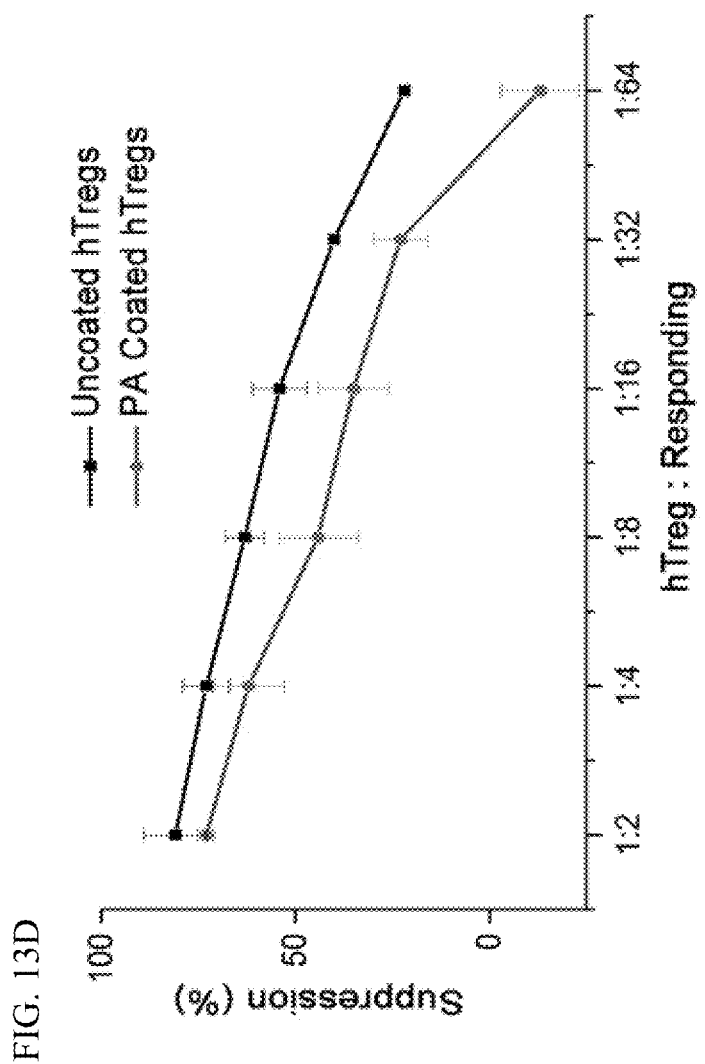
(FIG. 13D) The suppression profile of the uncoated hTregs and PA coated ($C_{16}V_3A_3E_3$) hTreg in the mixed lymphocyte reaction assay (n=4).
Figure 14A:
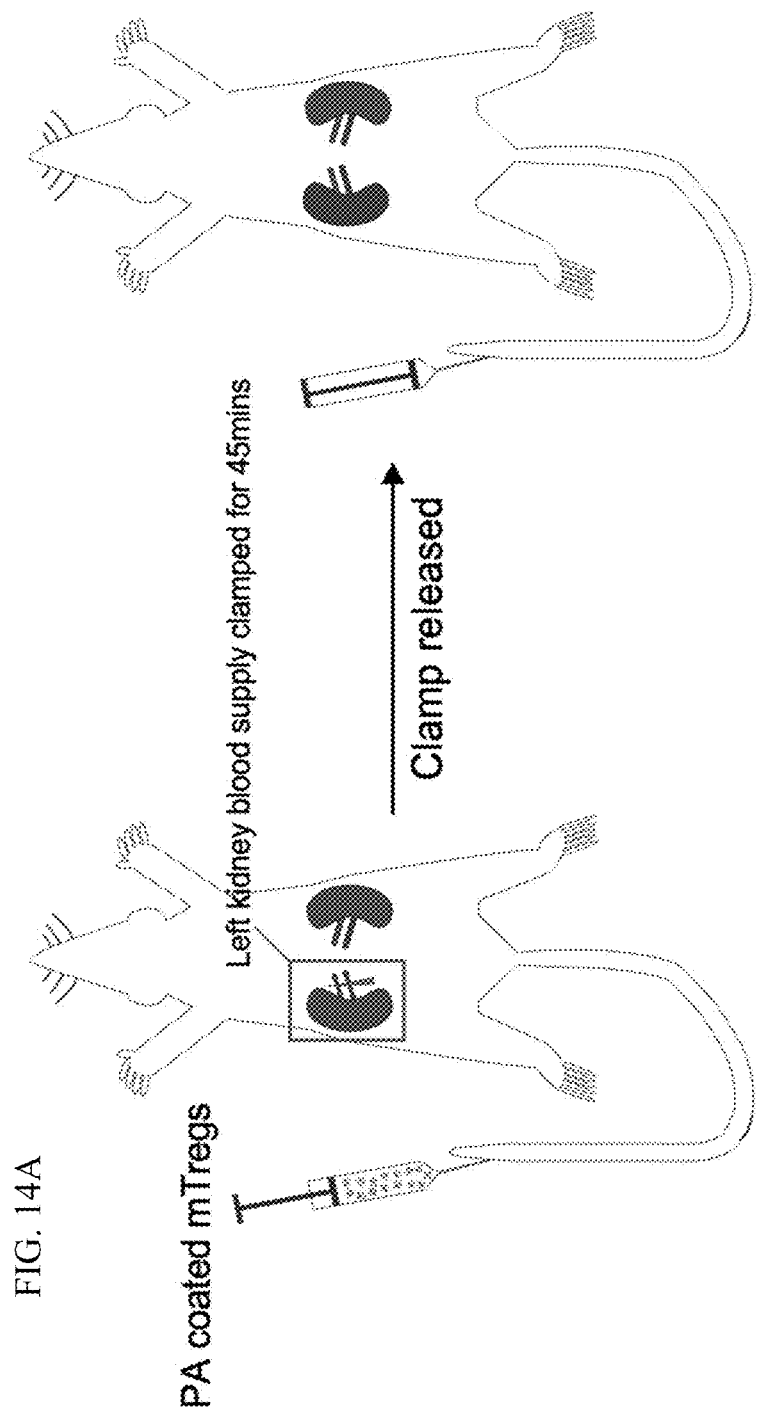
FIG. 14A-B. Fluorescent PA molecules from hTregs coating accumulated in injured kidney.
Figure 14B:
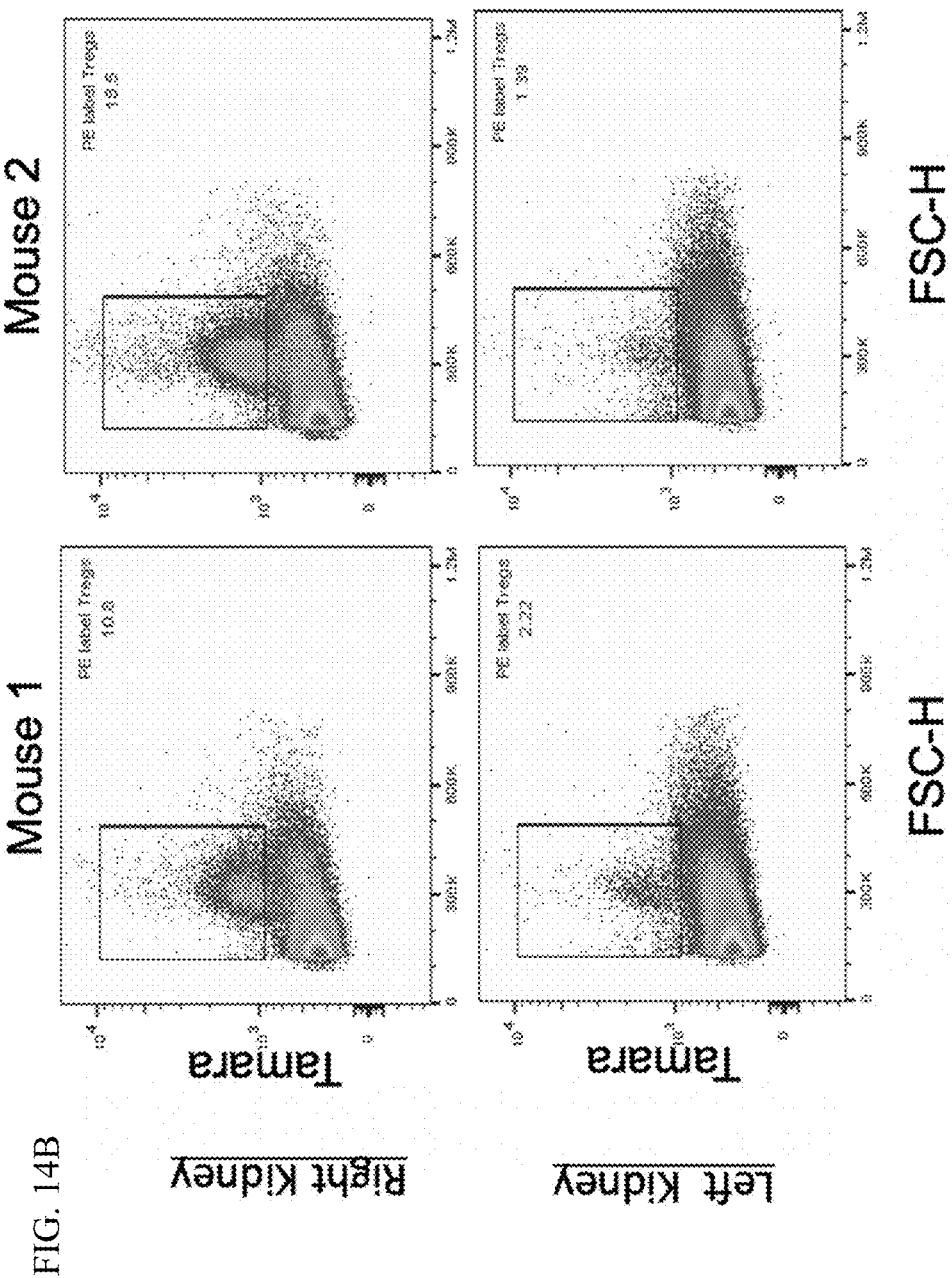
Figure 15A:
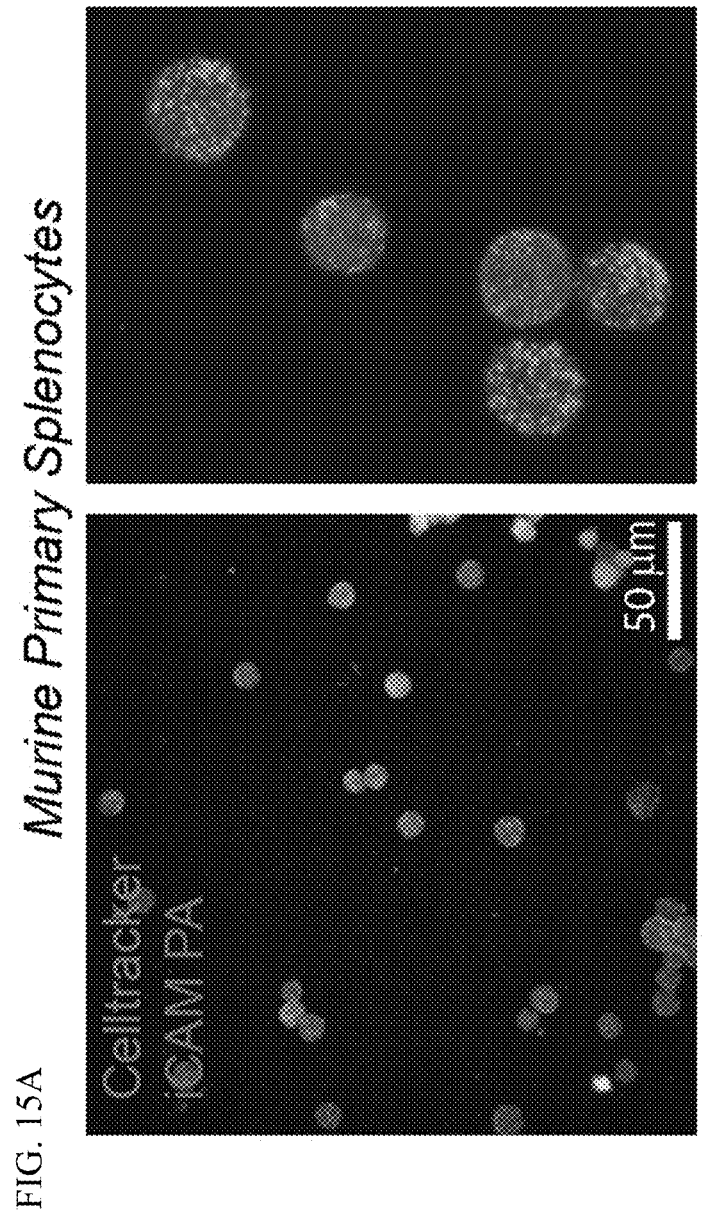
FIG. 15A-C.
Figure 15B:
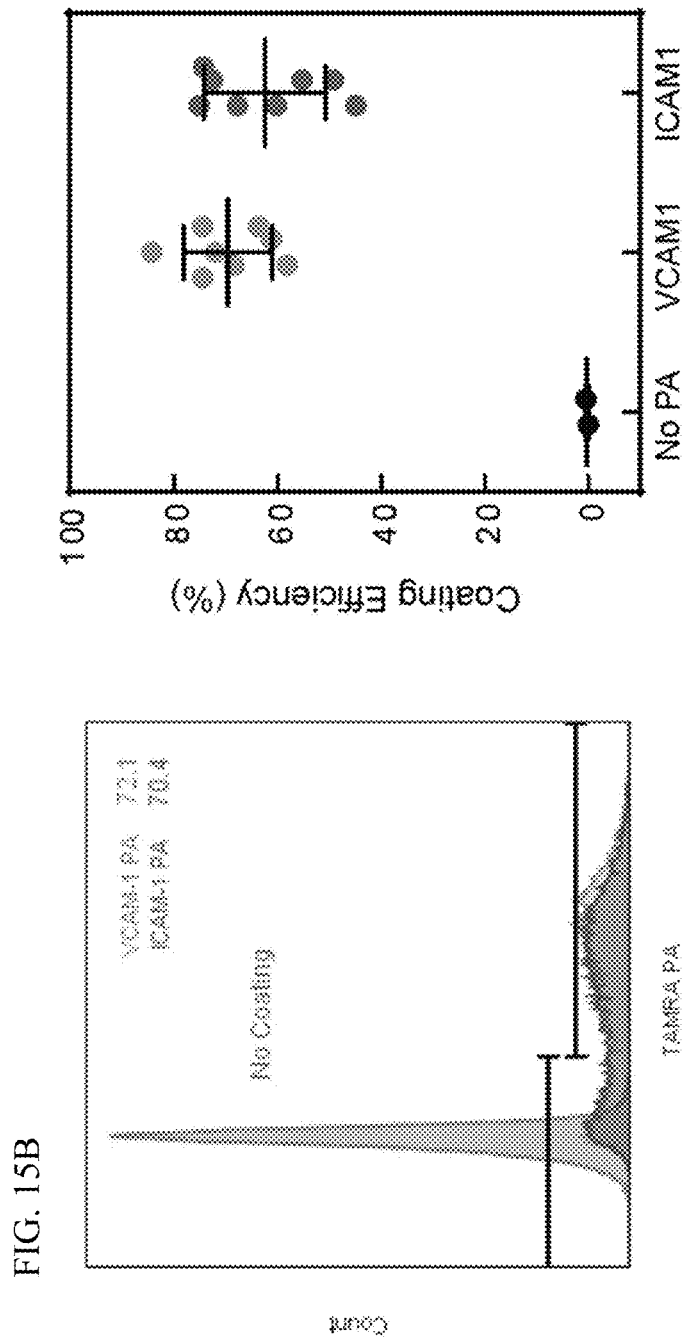
Figure 15C:
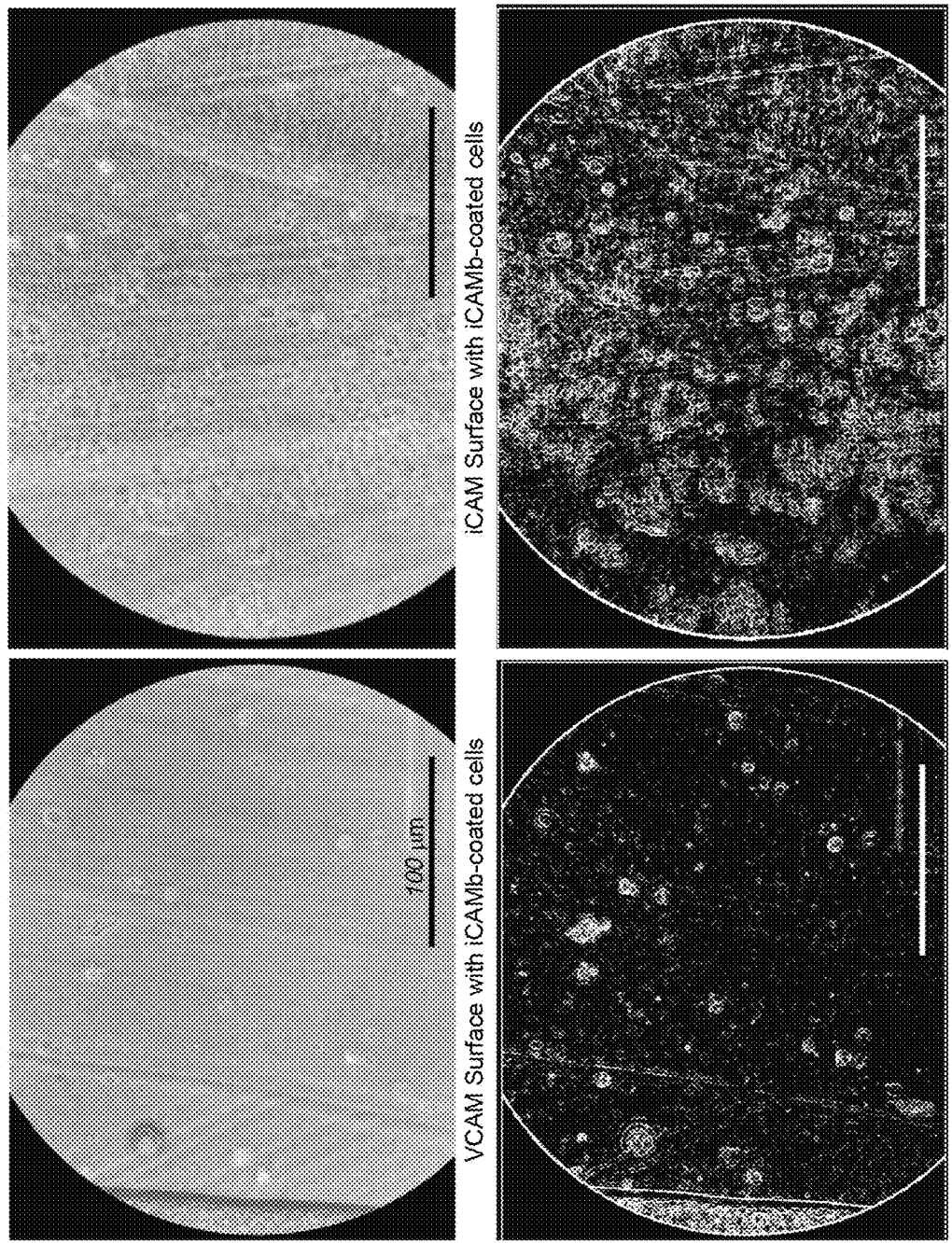

To assess whether the coatings impacted hTreg cell surface phenotypes, phenotypic expression of the standard hTreg markers CD3, CD4 and CD25[33] on uncoated hTregs and PA coated hTregs (FIG. 13A). 95% of the uncoated hTregs cells were positive for CD3, 89% positive for CD4 and 98% were positive for both CD4 and CD25 (FIG. 13B). The coated cells were phenotypically similar to the uncoated Tregs, with 96% positive for CD3, 90% positive for CD4 and 97% positive for both CD4 (FIG. 13B). The ability for antibodies to interact with the surface markers provided strong evidence for porosity of the cell coatings. In order to translate the cell coating method towards a new technology that improves hTreg therapy, it was next investigated whether the coating would not impact hTregs binding affinity towards endothelial markers of inflammation, such as VCAM1 protein[48]. An in vitro assay was performed in which cells were incubated in solution above discrete regions of recombinant human VCAM-1 coated on a tissue culture plate, based on a described protocol[49], and compared the affinities of uncoated hTregs to PA coated hTregs. The uncoated hTregs specifically targeted the VCAM1 surface (FIG. 13C). The backbone PA coated hTregs also retained function and specifically bound to inflammation marker VCAM1. However, cells coated using 1 mM backbone PA incubation solution had substantially reduced binding kinetics, likely due to cells a thicker PA coating. Based on flow cytometry we determined that a 500 µM coating solution efficiently coated cells, maintained a high viability, and based on mean fluorescence intensity produced thinner coatings (FIG. 3) Additionally, confocal images showed this coating concentration continued to form uniform cell coatings (FIG. 3D). It was therefore determined that thinner coatings produced by incubating hTregs in 500 µM solution have a greater relevance for translation of this technology to in vivo experiments. Finally, to confirm that backbone PAs would not interfere with cell function, it was examined whether coated hTreg cells retained their immunosuppressive activity when coated. The uncoated hTregs were compared to backbone coated Tregs in mixed lymphocyte reaction (MLR) suppression assays, although coated cells displayed a small reduction in suppressive capacity their overall function was retained. As an initial proof of concept experiment, mTregs were coated and injected into two mice with surgically introduced kidney ischemic reperfusion injuries. It was found the fluorescent molecules in the coating co-assembly accumulated at the injured kidney (FIG. 14).

This demonstrates that the coated cells as used in therapy accumulated at the injured organ while retaining their matrix coating.

CONCLUSIONS

Disclosed herein is a fast and simple nanofiber-based cell surface decoration method that is fully aqueous, allows the introduction of diverse biological signals, avoids the use of potentially toxic cationic materials, and does not require any specialized apparatus. After annealing, the nanostructures can be stored for days prior to use and the total time for coating is less than 30 minutes. The functional peptides could be added to the backbone PA molecular designs to allow targeted delivery of the therapeutic cells to a desired area within a subject. Here, the targeted delivery of the therapeutic cells was achieved using a specific protein (VCAM-1)-targeting peptide sequence. The coating procedures with or without the specific targeting moieties on the nanofibers did not negatively affect the natural function and the phenotypes of coated cells. Furthermore, using the artificially increased number of targeting molecules at the surface of cell complexes, the binding interaction between the cell complexes and the proteins could be achieved in a shorter time frame. The experimental results shown herein could be applied to therapeutic cells in various lineages, including but not limited to the T lymphocytes, myoblasts and stem cells. Accordingly, the technology disclosed herein allows for development of "systemic and targeted delivery" of the therapeutic cells, which holds a great potential in cell therapy mediated regenerative medicine.

Example 2

Organ transplants experience various stages of ischemia. These stages include the transient warm ischemic period following surgery from the donor, a cold ischemic environment when placed in the hypothermic preserving solution, and the warm ischemic period when implanted into the recipient. Revascularization of the organ triggers a cascade of cellular events that can sometimes lead to long-term graft dysfunction. One of these events is the initiation of the adaptive immune response.

Regulatory T-cells (Tregs) provide both pro-inflammatory and anti-inflammatory control over local immune cells. Tregs can attenuate innate immune responses in case of ischemia/reperfusion injury (IRI) through IL-10 mediated signaling. In addition, VCAM-1 and ICAM-1 are upregulated in the renal endothelium following IRI, and provide enhanced accumulation and migration of lymphocytes. Accordingly, delivering therapeutic agents to areas experiencing upregulation of VCAM-1 and/or ICAM-1 may be beneficial to combat elevated levels of inflammation, such as following organ transplant.

In this example, mouse Tregs were isolated from mice and coated with a fluorescent ICAM-1 targeting PA (also referred to herein as ICAM-1 binding PA or ICAMb PA) or a fluorescent VCAM-1 targeting PA (also referred to herein as VCAM-1 binding PA or VCAMb PA). As shown in FIG. 14A, an ischemic reperfusion surgery was performed on the kidneys of two mice. The blood supply to the left kidney was clamped for 45 minutes and then released to model an ischemic reperfusion injury. Mouse Tregs coated in PA ($C_{16}V_3A_3E_3$ containing the ICAM-1 or VCAM-1 targeting peptide) were injected systemically via mouse tail following clamp release. As shown in FIG. 14B, dissociated mouse kidney cells were analyzed by flow cytometry, and the tamara signal provided by the PA co-assembly was observed.

To further investigate the coating efficiency of the targeting PAs, murine primary splenocytes were isolated, coated with TAMRA-labeled ICAM-1 targeting PA, and visualized using confocal microscopy. As shown in FIG. 15A, primary splenocytes coated with TAMRA-labeled ICAM-1 targeting PA displayed high coating efficiency. Flow cytometry was subsequently performed to compare coating efficiency of ICAM-1 and VCAM-1 targeting PAs. As shown in FIG. 15B, flow cytometry of coated primary murine splenocytes displayed little difference between VCAM-1 and ICAM-1 targeting PA coating efficiency. Microfluidic flow experiments were subsequently performed (FIG. 15C), which demonstrated improved retention of coated lymphocytes on the target protein surface (ICAM-1 targeting PA on ICAM surface, right panels), while non-specific interactions were minimal for off-target proteins (VCAM-1 targeting PA on ICAM surface, left panels). This can be visualized through both light microscopy (top) and processed images highlighting bound cell edges (bottom).

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

The invention claimed is:

1. A cell comprising a plurality of peptide amphiphiles coating at least a portion of an outer surface of the cell, wherein each peptide amphiphile comprises a hydrophobic tail comprising an 8-24 carbon alkyl chain ($C_{8-24}$), a structural peptide segment comprising $V_3A_3$ (SEQ ID NO: 6), a charged peptide segment comprising EE, EEE, or EEEE (SEQ ID NO: 4), and a targeting moiety comprising VHPKQH (SEQ ID NO: 1), Cyclo(1,12)Pen-ITDGEATDSGC (SEQ ID NO: 18) (cLABL), or RDVLPGT (SEQ ID NO: 2), wherein the plurality of peptide amphiphiles coat at least 75% of the outer surface of the cell.

2. The cell of claim 1, wherein the targeting moiety is attached to the charged peptide segment by a linker.

3. The cell of claim 2, wherein the linker comprises the amino acid sequence GSG.

4. The cell of claim 1, wherein the plurality of peptide amphiphiles coat at least 90% of the outer surface of the cell.

5. The cell of claim 1, wherein the cell is a regulatory T-cell.

6. The cell of claim 1, wherein the plurality of peptide amphiphiles coat the portion of the outer surface of the cell by entangling with microvilli on the cell surface.

7. The cell of claim 1, wherein the plurality of peptide amphiphiles coating the portion of the outer surface of the cell are nanofibers.

8. The cell of claim 1, wherein the cell coated with the plurality of peptide amphiphiles is viable.

9. The cell of claim 1, wherein the cell coated with the plurality of peptide amphiphiles retains its phenotype and function compared to the cell without coating.

10. The cell of claim 1, wherein the plurality of peptide amphiphiles coat the at least 75% of the outer surface of the cell within 5 minutes of contacting the cell with the plurality of peptide amphiphiles.

11. The cell of claim 9, wherein the plurality of peptide amphiphiles coat the at least 75% of the outer surface of the cell within 1 minute of contacting the cell with the plurality of peptide amphiphiles.

12. A composition comprising the cell of claim 1.

13. A method of treating and/or preventing transplant rejection in a subject, comprising providing to the subject the composition of claim 12.

* * * * *